(12) United States Patent
Ow et al.

(10) Patent No.: US 8,129,598 B2
(45) Date of Patent: *Mar. 6, 2012

(54) DNA RECOMBINATION IN EUKARYOTIC CELLS BY THE BACTERIOPHAGE PHIC31 RECOMBINATION SYSTEM

(75) Inventors: David W. Ow, Hercules, CA (US); Richard Calendar, Berkeley, CA (US); Lynn Thomason, Albany, CA (US)

(73) Assignees: The Regents of the University of California, Oakland, CA (US); The United States of America as represented by the Secretary of Agriculture, Washington, DC (US)

( * ) Notice: Subject to any disclaimer, the term of this patent is extended or adjusted under 35 U.S.C. 154(b) by 927 days.

This patent is subject to a terminal disclaimer.

(21) Appl. No.: 10/721,980

(22) Filed: Nov. 24, 2003

(65) Prior Publication Data

US 2005/0054106 A1 Mar. 10, 2005

Related U.S. Application Data

(63) Continuation of application No. 09/620,800, filed on Jul. 21, 2000, now Pat. No. 6,746,870.

(60) Provisional application No. 60/145,469, filed on Jul. 23, 1999.

(51) Int. Cl.
*C12N 5/04* (2006.01)

(52) U.S. Cl. .................. 800/317.3; 435/254.2; 435/462; 435/468; 435/471; 435/419; 435/235.1; 435/475; 435/410

(58) Field of Classification Search ........................ None
See application file for complete search history.

(56) References Cited

U.S. PATENT DOCUMENTS

| | | | |
|---|---|---|---|
| 5,190,871 A | | 3/1993 | Cox et al. |
| 5,434,066 A | * | 7/1995 | Bebee et al. ................. 435/475 |
| 5,527,695 A | | 6/1996 | Hodges et al. |
| 5,744,336 A | | 4/1998 | Hodges et al. |
| 5,888,732 A | * | 3/1999 | Hartley et al. .................... 435/6 |
| 5,910,415 A | | 6/1999 | Hodges et al. |
| 6,110,736 A | | 8/2000 | Hodges et al. |
| 6,114,600 A | | 9/2000 | Ow et al. |
| 6,143,530 A | * | 11/2000 | Crouzet et al. ............. 435/91.42 |
| 6,175,058 B1 | | 1/2001 | Baszczynski et al. |
| 6,187,994 B1 | | 2/2001 | Baszczynski et al. |
| 6,262,341 B1 | | 7/2001 | Baszczynski et al. |
| 6,632,672 B2 | | 10/2003 | Calos |
| 6,746,870 B1 | * | 6/2004 | Ow et al. ...................... 435/477 |
| 6,808,925 B2 | | 10/2004 | Calos |
| 6,936,747 B2 | * | 8/2005 | Ow .............................. 800/294 |
| 2002/0123145 A1 | | 9/2002 | Ow |
| 2005/0009182 A1 | | 1/2005 | Ow |
| 2006/0046294 A1 | | 3/2006 | Ow et al. |

FOREIGN PATENT DOCUMENTS

| | | |
|---|---|---|
| WO | WO 97/37012 | 10/1997 |
| WO | WO 99/18222 A | 4/1999 |
| WO | WO 99/25821 | 5/1999 |
| WO | WO 00/11155 A | 3/2000 |
| WO | WO 00/60091 | 10/2000 |
| WO | WO 01/07572 A3 | 2/2001 |

OTHER PUBLICATIONS

Sigmund, C.D. 2000. Arterioscler Thromb Vasc Biol.20:1425-1429.*
Wall, R.J. 1996. Theriogenology 45:57-68.*
Bradley et al. 1992.Bio/technology 10:534-539.*
Mullins et al. 1996 Clin. Invest. 97:1557-1560.*
Thorpe et al. PNAS vol. 95 1998 pp. 5505-5510.*
Bradley et al., Bio/Technology, vol. 10 (1992), pp. 534-539.*
Campbell et al., Theriogenology, vol. 47 (1997), pp. 63-72.*
Mullins et al., Journal of Clinical Investigations, vol. 97, (1996) pp. 1557-1560.*
Crellin et al., J. Bacteriol., vol. 179, 1997, pp. 5148-5156.*
Carrasco et al., Genes. Dev., vol. 8, 1994, pp. 74-83.*
Sato et al., J. Bacteriol. vol. 172, pp. 1092-1098.*
Benton, B., et al, "Signal-Mediated Import of Bacteriophage T7 RNA Polymerase into the *Saccharomyces cerevisiae* Nucleus and Specific Transcription of Target Genes," American Society for Microbiology; *Molecular and Cellular Biology*, 1990, vol. 10, No. 1, pp. 353-360.
Lorbach, E., et al., "Site Specific Recombination in Human Cells Catalyzed by Phage Integrase Mutants," JMB, 2006, doi:10:1006/jmbi.2000.3532, vol. 296, pp. 1175-1181.
Reiss, B., et al., "RecA protein stimulates homologous recombination in plants," Proc. Natl. Acad. Sci. , 1996, vol. 93, pp. 3094-3098.
Reiss, B., et al., "RecA stimulates sister chromatid exchange and the fidelity of double-strand break repair, but no gene targeting, in plants transformed by Agrobacterium," PNAS, 2000, vol. 97 No. 7, 3358-3663.
Albert et al., "Site-specific integration of DNA into wild-type and mutant lox sites placed in the plant genome," Plant J., 7:649-59 (1995).
Alonso et al., "The *Bacillus subtilis* Histone-like Protein Hbsu Is Required for DNA Resolution and DNA Inversion Mediated by the β Recombinase of Plasmid pSM19035," J. Biol. Chem., 270:2938-45 (1995).
Araki et al., "Site-specific Recombinase, R, Encoded by Yeast Plasmid pSR1," J. Mol. Biol., 225(1):25-37 (1992).
Araki et al., "Targeted integration of DNA using mutant lox sites in embryonic stem cells," Nucleic Acids Res., 25:868-72 (1997).
Argos et al. "The integrase family of site-specific recombinases: regional similarities and global diversity," EMBO J. 5(2):433-44 (1986).

(Continued)

*Primary Examiner* — James S Ketter
(74) *Attorney, Agent, or Firm* — Kilpatrick Townsend & Stockton LLP

(57) ABSTRACT

This invention provides methods for obtaining specific and stable integration of nucleic acids into eukaryotic cells. The invention makes use of site-specific recombination systems that use prokaryotic recombinase polypeptides, such as the ΦC31 integrase, that can mediate recombination between the recombination sites, but not between hybrid recombination sites that are formed upon the recombination. Thus, the recombination is irreversible in the absence of additional factors. Eukaryotic cells that contain the recombinase polypeptides, or genes that encode the recombinases, are also provided.

20 Claims, 5 Drawing Sheets

OTHER PUBLICATIONS

Bannam et al., "Molecular genetics of the chloramphenicol-resistance transposon Tn4451 from *Clostridium perfringens*: the TnpX site-specific recombinase excises a circular transposon molecule," Mol. Microbiol. 16(3):535-551 (1995).
Baubonis and Sauer, "Genomic targeting with purified Cre recombinase," Nucl. Acids Res., 21:2025-29 (1993).
Bayley et al., "Exchange of gene activity in transgenic plants catalyzed by the Cre-lox site-specific recombination system," Plant Mol. Biol., 18:353-61 (1992).
Becker et al., "Fertile transgenic wheat from microprojectile bombardment of scutellar tissue," The Plant Journal, 5(2):299-307 (1994).
Bethke and Sauer, "Segmental genomic replacement by Cre-mediated recombination: genotoxic stress activation of the p53 promoter in single-copy transformants," Nucleic Acids Res., 25:2828-34 (1997).
Bhattacharyya et al., "Reduced variation in transgene expression from a binary vector with selectable markers at the right and left T-DNA borders," Plant J., 6:957-68 (1994).
Carrasco et al., "*Anabaena xisF* gene encodes a developmentally regulated site-specific recombinase," Genes & Dev. 8:74-83 (1994).
Choi et al., "A new approach for the identification and cloning of genes: the pBACwich system using Cre/lox site-specific recombination," Nucl. Acids Res., 28:e19(i-vii) (2000).
Cluster et al., "Details of T-DNA structural organization from a transgenic Petunia population exhibiting co-suppression," Plant Molecular Biology, 32:1197-1203 (1996).
Corneille et al., "Efficient elimination of selectable marker genes from the plastid genome by the CRE-lox site-specific recombination system," The Plant J., 27:171-78 (2001).
Crellin and Rood, "The Resolvase/Invertase Domain of the Site-Specific Recombinase TnpX Is Functional and Recognizes a Target Sequence That Resembles the Junction of the Circular Form of the *Clostridium perfringens* Transposon Tn4451," J. Bacteriol. 179(16):5148-5156 (1997).
Crisona et al., "Processive Recombination by Wild-type Gin and an Enhancer-independent Mutant," J. Mol. Biol., 243(3):437-57 (1994).
Davies et al., "Somatic and germinal inheritance of an FLP-mediated deletion in transgenic tobacco," J. of Experimental Botany, 50:1447-56 (1999).
Day et al., "Transgene integration into the same chromosome location can produce alleles that express at a predictable level, or alleles that are differentially silenced," Genes and Development, 14:2869-80 (2000).
De Buck et al., "Transgene silencing of invertedly repeated transgenes is released upon deletion of one of the transgenes involved," Plant Mol. Biol, 46:433-45 (2001).
Diaz et al., "New Insights into Host Factor Requirements for Prokaryotic β-Recombinase-mediated Reactions in Mammalian Cells," J. Biol. Chem., 276:16257-64 (2001).
Diaz et al., "The Prokaryotic β-Recombinase Catalyzes Site-specific Recombination in Mammalian Cells," J. Biol. Chem. 274(10):6634-6640 (1999).
Feng et al., "Site-specific Chromosomal Integration in Mammalian Cells: Highly Efficient CRE Recombinase-mediated Cassette Exchange," J. Mol. Biol., 292:779-85 (1999).
Finkel and Johnson, "The Fis protein: it's not just for DNA inversion anymore," Mol. Microbiol. 6(22):3257-3265 (1992).
Forsburg, S.L. (1993) Nucleic Acids Res 21:2955-2956.
Friedman, "Integration Host Factor: A Protein for All Reasons," Cell 55:545-554 (1988).
Gleave et al., "Selectable marker-free transgenic plants without sexual crossing: transient expression of cre recombinase and use of a conditional lethal dominant gene," Plant Mol. Biol., 40:223-35 (1999).
Grimm et al. (1988) Mol. Gen. Genet. 215:81-86.
Groth et al., "A phage integrase directs efficient site-specific integration in human. cells," PNAS, 97:5995-6000 (2000).
Hajdukiewicz et al., "Multiple pathways for Cre/lox-mediated recombination in plastids," The Plant J., 27:161-170 (2001).
Hatfull & Grindley (1988) "Resolvases and DNA-invertases: a family of enzymes active in site-specific recombination" Chapter 11 in *Genetic Recombination*, eds. Kucherlipati, R., & Smith, G.R. (Am. Soc. Microbiol., Washington, DC), pp. 357-396 (1998).
Hohn et al., "Elimination of selection markers from transgenic plants," Current Opinion in Biotechnology, 12:139-43 (2001).
Howe et al., "Cis-Effects of Heterochromatin and Euchromatic Gene Activity in *Drosophila melanogaster*," Genetics, 140:1033-45(1995).
Hucl et al., "Impact of marker genes on agronomic performance of transgenic spring wheat," 3:189, In: Slinkand ed. Proc 9th Int Wheat Genet Symp. U. Sask.Ext. Press, Saskatoon, Sask, Canada, (1998).
Iglesias et al., "Molecular and Cytogenetic Analyses of Stably and Unstably Expressed Transgene Loci in Tobacco," The Plant Cell, 9:1251-1264 (1997).
Iyer et al., "Transgene silencing in moncots," Plant Mol. Biol., 43:323-46 (2000).
Jones, R. (Editor) *Annual Review of Plant Physiology and Plant Molecular Biology*, vol. 47 (1996).
Jorgensen, "Cosuppression, Flower Color Patterns, and Metastable Gene Expression States," Science, 268:686 (1995).
Kaeppler et al., "Epigenetic aspects of somaclonal variation in plants," Plant Mol. Biol., 43:179-88 (2000).
Keeney & Boeke (1994) Genetics 136:849-856.
Kilby et al., "Controlled induction of GUS marked clonal sectors in *Arabidopsis*," J. of Experimental Botany, 51:853-63 (2000).
Kluth et al., "Inheritance and expression of transgenes in hexaploid wheat," 3:192, in: Slinkland et al., Proc. 9th Wheat Gen. Sym. (1998).
Kohli et al., "Transgene organization in rice engineered through direct DNA transfer supports a two-phase integration mechanism mediated by the establishment of integration hot spots," Proc. Natl. Sci. USA, 95:7203-7208 (1998).
Kolb and Siddell, "Genomic targeting of a bicistronic DNA fragment by Cre-mediated site-specific recombination," Gene, 203:209-16 (1997).
Kolot et al., "Site-specific recombination in mammalian cells expressing the Int Recombinase of bacteriophage HK022," Mol. Biol. Reports, 26:207-13 (1999).
Kononov et al., "Integration of T-DNA binary vector 'backbone' sequences into the tobacco genome: evidence for multiple complex patterns of integration," The Plant Journal, 11(5):945-957 (1997).
Kooter et al., "Trans-inactivation of gene expression in plants," Current Opinion in Biotechnology, 4:166-171 (1993).
Kuhstoss and Rao, "Analysis of the Integration Function of the Streptomycete Bacteriophage ΦC31," J. Mol. Biol., 222:897-908 (1991).
Kutsukake et al., "A gene for DNA invertase and an invertible DNA in *Escherichia coli* K-12," Gene, 34(2-3):343-50 (1985).
Landy, "Dynamic, Structural, and Regulatory Aspects of λ Site-Specific Recombination," Ann. Rev. Biochem., 58:913-949 (1989).
Loessner et al., "Complete nucleotide sequence, molecular analysis and genome structure of bacteriophage A118 of *Listeria monocytogenes*: implications for phage evolution," Mol. Microbiology, 35:324:40 (2000).
Loonstra et al., "Growth inhibition and DNA damage induced by Cre recombinase in mammalian cells," PNAS, 98:9209-14 (2001).
Lyznik et al., "Activity of yeast FLP recombinase in maize and rice protoplasts," Nucleic Acids Res., 21:969-75 (1993).
Lyznik et al., "FLP-mediated recombination of FRT sites in the maize genome," Nucleic Acids Res., 24(19):3784-9 (1996).
Maeser and Kahmann, "The Gin recombinase of phase Mu can catalyse site-specific recombination in plant protoplasts," Mol. Gen. Genet. 230:170-176 (1991).
Matsuura et al., "The sre Gene (ORF469) Encodes a Site-Specific Recombinase Responsible for Integration of the R4 Phage Genome," J. Bacteriol. 178(11):3374-3376 (1996).
Matzke et al., "Transgene silencing by the host genome defense: implications for the evolution of epigenetic control mechanisms in plants and vertebrates," Plant Mol. Biol., 43:401-15 (2000).
Maundrell, K. (1993) Gene 123:127-130.
Medberry et al., "Intra-chromosal rearrangements generated by Cre-lox site-specific recombination," Nucleic Acids Res., 23:485-90 (1995).
Meyer, "Transcriptional transgene silencing and chromatin components," Plant Mol. Biol., 43:221-34 (2000).

Muskens et al., "Role of inverted DNA repeats in transcriptional and post-transcriptional gene silencing," Plant Mol. Biol., 43:243-60 (2000).

Nehra et al., "Self-fertile transgenic wheat plants regenerated from isolated scutellar tissues following microprojectile bombardment with two distinct gene constructs," The Plant Journal, 5(2):285-297 (1994).

O'Gorman et al., "Recombinase-Mediated Gene Activation and Site-Specific Integration in Mammalian Cells," Science, 251:1351-55 (1991).

Ohi et al. (1996) Gene 174:315-318.

Onouchi et al., Visualization of site-specific recombination catalyzed by a recombinase from Zygosaccharomyces rouxii in Arabidopsis thaliana, Mol. Gen. Genet. 247: 653-660 (1995).

Ow and Ausubel, "Conditionally Replicating Plasmid Vectors That Can Integrate into the Klebsiella pneumoniae Chromosome via Bacteriophage P4 Site-Specific Recombination," J. Bacteriol. 155(2): 704-713 (1983).

Ow, "Recombinase-directed chromosome engineering in plants," Current Opinion in Biotechnology, 7:181-86 (1996).

Ow, "The right chemistry for marker gene removal?," Nature Biotechnology, 19:115-6 (2001).

Ow, "Recombinase-directed plant transformation for the post-genomic era," Plant Molecular Biology, 48:183-200 (2002).

Pawlowski et al., "Transgene Inheritance in Plants Genetically Engineered by Microprojectile Bombardment," Molecular Biology, 6:17-30 (1996).

Pesehke and Phillips, "Genetic Implications of Somaclonal Variation in Plants," Advances in Genetics, 30:41-75 (1992).

Qin et al., "Cre recombinase-mediated site specific recombination between plant chromosomes," Proc. Natl. Acad. Sci., 91:1706-10 (1994).

Qin et al., "Site-specific cleavage of chromosomes in vitro through Cre-lox recombination," Nucleic Acids Res., 23:1923-7 (1995).

Sabelli et al., "Nucleic Acid Blotting and Hybridisation," Methods In Plant Biochemistry, 10:79 (1993).

Sadowski, "Site-specific genetic recombination: hops, flips, and flops," FASEB J. 7:760-767 (1993).

Sadowski, "Site-Specific Recombinases: Changing Partners and Doing the Twist," J. Bacteriol. 165(2): 341-347 (1986).

Sato et al., "The cisA Cistron of Bacillus subtilis Sporulation Gene spoIVC Encodes a Protein Homologous to a Site-Specific Recombinase," J. Bacteriol. 172(2):1092-1098 (1990).

Sauer, Site-specific recombination: developments and applications, Curr. Opin. in Biotechnol. 5:521-527 (1994).

Schmidt et al., "Illegitimate Cre-dependent chromosome rearrangements in transgenic mouse spermatids," PNAS, 97:13702-7 (2000).

Seibler and Bode, "Double-Reciprocal Crossover Mediated by FLP-Recombinase: A Concept and an Assay," Biochem., 36:1740-7 (1997).

Seibler et al., "DNA Cassette Exchange in ES Cells Mediated by FLP Recombinase: An Efficient Strategy for Repeated Modification of Tagged Loci by Marker-Free Constructs," Biochemistry, 37:6229-34 (1998).

Srivastava and Ow, "Single-copy primary transformants of maize obtained through the co-introduction of a recombinase-expressing construct," Plant Mol. Biol., 46:561-566 (2001).

Srivastava et al., "A General Strategy For Introducing A Single Copy Transgene Into Plant Genome: Demonstration Of Single Copy Transgenic Lines Of Wheat (Triticum aestivum)," Published Internet Nov. 1997.

Srivastava et al., "Molecular characterization of the fate of transgenes in transformed wheat (Triticum aestivum L.)," Theor Appl Genet, 92:1031-1037 (1996).

Srivastava et al., "Single-copy transgenic wheat generated through the resolution of complex integration patterns," Proc. Natl. Acad. Sci. USA, 96:11117-11121 (1999).

Stark et al., Catalysis by site-specific recombinases, Trends Genetics 8(12):432-439 (1992).

Stavenhagen and Zakian, "Internal tracts of telomeric DNA act as silencers in Saccharomyces cerevisiae," Genes and Dev., 8:1411-22 (1994).

Stragier et al., "Chromosomal Rearrangement Generating a Composite Gene for a Developmental Transcription Factor," Science 243:507-512 (1989).

Thomason et al., "Gene insertion and replacement in Schizosaccharomyces pombe mediated by the Streptomyces bacteriophage ΦC31 site-specific recombination system," Mol. Genet. Genomics, 265:1031-8 (2001).

Thorpe and Smith, "In vitro site-specific integration of bacteriophage DNA catalyzed by a recombinase of the resolvase/invertase family," Proc. Nat'l. Acad. Sci. USA 95:5505-5510 (1998).

Thyagarajan et al., Mammalian genomes contain active recombinase recognition sites, GENE, 244:47-54 (2000).

Thyagarajan et al., "Site-Specific Genomic Integration in Mammalian Cells Mediated by Phage ΦC31 Integrase," Mol. and Cell. Biol., 21:3926-34 (2001).

Tominaga et al., "Site-Specific Recombinase Genes in Three Shigella Subgroups and Nucleotide Sequences of a pinB Gene and an Invertible B Segment from Shigella boydii," J. Bacteriol., 173(13):4079-87 (1991).

Vasil et al., "Rapid Production of Transgenic Wheat Plants by Direct Bombardment of Cultured Immature Embryos," Bio/Technology, 11:1553 (1993).

Vergunst and Hooykaas, "Cre/lox-mediated site-specific integration of Agrobacterium T-DNA in Arabidopsis thaliana by transient expression of cre," Plant Mol. Biol., 38:393-406 (1998).

Vergunst et al., "Cre/lox-mediated recombination in Arabidopsis: evidence for transmission of a translocation and a deletion event," Chromosoma, 109:287-97 (2000).

Vergunst et al., "Site-specific integration of Agrobacterium T-DNA in Arabidopsis thaliana mediated by Cre recombinase," Nucleic Acids Res., 26:2729-34 (1998).

Vergunst et al., "VirB/D4-Dependent Protein Translocation from Agrobacterium into Plant Cells," Science, 290:979-82 (2000).

Voziyanov et al., "A general model for site-specific recombination by the integrase family recombinases," Nucl. Acids Res. 27(4):930-941 (1999).

Wallrath and Elgin, "Position effect variegation in Drosophila is associated with an altered chromatin structure," Genes and Dev., 9:1263-77 (1995).

Weeks et al., "Rapid Production of Multiple Independent Lines of Fertile Transgenic Wheat (Triticum aestivum)," Plant Physiol., 102:1077-1084 (1993).

Weisberg & Landy (1983) "Site-specific Recombination in Phage Lambda" in Lambda II, eds. Hendrix et al. (Cold Spring Harbor Laboratory, Cold Spring Harbor NY) pp. 211-250 (1983).

Zuo et al., "Chemical-regulated, site-specific DNA excision in transgenic plants," Nature Biotechnology, 19:157-61 (2001).

Belteki et al., "Site-specific cassette exchange and germline transmission with mouse ES cells expressing C31 integrase," Nature Biology (2003) 21:321-334.

Dale et al., "Gene transfer with subsequent removal of the selection gene from the host genome," Proc. Natl. Acad. Sci. USA (1991) 88:210558-10562.

Dale et al., "Intra- and intermolecular site-specific recombination in plant cells mediated by bacteriophage P1 recombinase," Gene (1990) 91:79-85.

Ferl et al., "Genome organization and expression," In: Biochemistry & Molecular Biology of Plants (Eds) Buchanan, Gruissem, Jones (2000) Chapter 7, p. 322 last paragraph.

Gilbertson et al., "Cre/lox mediated marker gene excision in transgenic crop plants," Conference on In Vitro Technology, St Louis. In: In vitro Cellular and Development Biology Animal, (2001) 37(3 part 2):26A, P-1019.

Golic t al., "FLP-mediated DNA mobilization to specific target sites in Drosophila chromosomes," Nucleic Acids Research (1997) 25(18):3665-3671.

Grainge et al., "The integrase family of recombinases: organization and function of the active site," Molecular Microbiology (1991) 33(3):449-456.

Hasty et al., "Target frequency and integration pattern for insertion and replacement vectors in embryonic stem cells," Molecular & Cellular Biology (1991) 11(9):4509-4517.

Hasty et al., "The length of homology required for gene targeting in embryonic stem cells," Molecular & Cellular Biology (1991) 11(11):5586-5591.

Holliday, "A mechanism for gene conversion in fungi," Genet. Res., Camb. (1964) 5:282-304.

Lorbach et al., "Site-specific recombination in Human cells catalyzed by phage λ, integrase mutants," J. Mol. Biol. (2000) 296:1175-1181.

Meyer et al., "Homology-dependent gene silencing in plants," Annu. Rev. Plant Physiol. Plant Mol. Biol. (1996) 47:23-48.

Ow, et al., "Genome manipulation through site-specific recombination," Critical Reviews in Plant Sciences (1995) 14(3):239-261.

Schwikardi et al., "Site-specific recombination in mammalian cells catalyzed by γδresolvase mutants: implications for the topology of episomal DNA," FEBS Letters (2000) 471:147-150.

Srivastava et al., "Biolistic mediated site-specific integration in rice," Molecular Breeding (2001) 8:345-350.

Szostak et al., "The double-strand-break repair model for recombination," Cell (1983) 33:25-35.

Tirumalai et al., "The catalytic domain of λ, site-specific recombinase," Proc. Natl. Acad. Sci. USA (1997) 94:6104-6109.

* cited by examiner

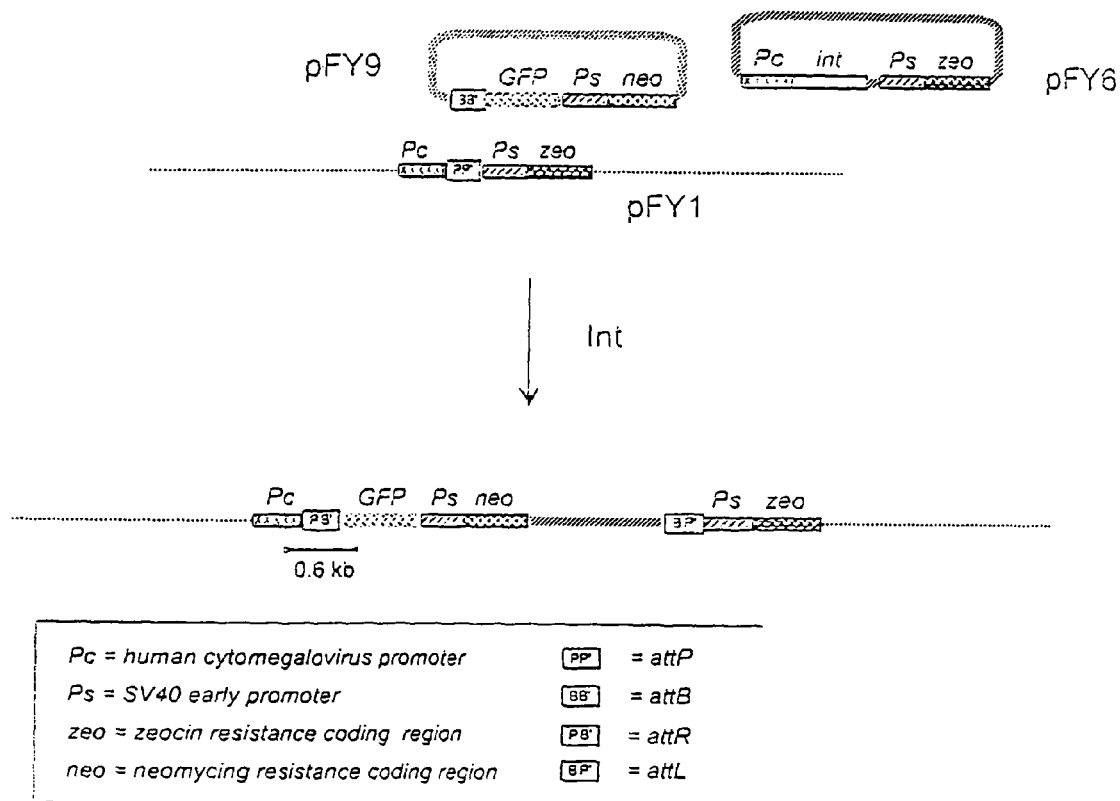

Figure 3

Transgene integration in CHO cell line
hygromycin resistance from *attB* x *attP* recombination pBSK-hpt (no attP)
pFY17 (attP-90)
pFY19 (attP-50)
pFY20 (attP-32)

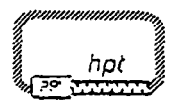

↓ Int

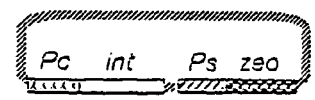 pFY6 pFY12 (attB-90)
pFY14 (attB-50)
pFY15 (attB-30)

0.8 kb

| Pc = human cytomegalovirus promoter | | |
|---|---|---|
| Ps = SV40 early promoter | PP' | = attP |
| zeo = zeocin resistance coding region | BB' | = attB |
| neo = neomycing resistance coding region | PB' | = attR |
| hpt = hygromycin resistance coding region | BP' | = attL |
| lacZ = beta-galactosidase coding region | | |

Excision of DNA from tobacco genome

Integration of DNA into the tobacco genome

SEQUENCE LISTING

<160> NUMBER OF SEQ ID NOS: 8

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:ura4 primer

<400> SEQUENCE: 1
gtcaaaaagt ttcgtcaata tcac                                          24

```
<210> SEQ ID NO 2
<211> LENGTH: 102
<212> TYPE: DNA
<213> ORGANISM: Artificial Sequence
<220> FEATURE:
<223> OTHER INFORMATION: Description of Artificial Sequence:90 bp of the
      attB sequence contained in pFY12 flanked by
      HindIII and KpnI sites

<400> SEQUENCE: 2
aagcttgacg gtctcgaagc cgcggtgcgg gtgccagggc gtgcccttgg gctccccggg      60
cgcgtactcc acctcaccca tctggtccat catgatggta cc                       102

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence:50 bp of the
      attB sequence contained in pFY14 flanked by
      HindIII and KpnI sites

<400> SEQUENCE: 3
aagcttgcgg gtgccagggc gtgcccttgg gctccccggg cgcgtactcc acctcatggt      60
acc                                                                   63

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence:30 bp of the
      attB sequence contained in pFY15 flanked by
      HindIII and KpnI sites

<400> SEQUENCE: 4
aagcttccag ggcgtgccct tgggctcccc gggcgcatgg tacc                       44

<210> SEQ ID NO 5
<211> LENGTH: 102
<212> TYPE: DNA
<213> ORGANISM: Artificial Sequence
<220> FEATURE:
<223> OTHER INFORMATION: Description of Artificial Sequence:90 bp of the
      attP sequence contained in pFY17 flanked by SacI
      and BamHI sites

<400> SEQUENCE: 5
gagctcgaag cggttttcgg gagtagtgcc ccaactgggg taacctttga gttctctcag      60
ttgggggcgt agggtcgccg acatgacaca aggggtggat cc                       102

<210> SEQ ID NO 6
<211> LENGTH: 62
<212> TYPE: DNA
<213> ORGANISM: Artificial Sequence
<220> FEATURE:
<223> OTHER INFORMATION: Description of Artificial Sequence:50 bp of the
      attP sequence contained in pFY19 flanked by SacI
      and BamHI sites

<400> SEQUENCE: 6
gagctctgcc ccaactgggg taacctttga gttctctcag ttgggggcgt agggtcggat      60
cc                                                                    62

<210> SEQ ID NO 7
<211> LENGTH: 42
```

```
<212> TYPE: DNA
<213> ORGANISM: Artificial Sequence
<220> FEATURE:
<223> OTHER INFORMATION: Description of Artificial Sequence:32 bp of the
      attP sequence contained in pFY20 flanked by SacI
      and BamHI sites

<400> SEQUENCE: 7
gagctcactg gggtaacctt tgagttctct cagttgggat cc                         42

<210> SEQ ID NO 8
<211> LENGTH: 89
<212> TYPE: DNA
<213> ORGANISM: Artificial Sequence
<220> FEATURE:
<223> OTHER INFORMATION: Description of Artificial Sequence:synthetic
      oligonucleotide containing a Kozack sequence and
      the N-terminal amino acid coding sequences of the
      integrase gene

<400> SEQUENCE: 8
gggcccgcca cgatgacaca aggggttgtg accggggtgg acacgtacgc gggtgcttac      60
gaccgtcagt cgcgcgagcg cgagaattc                                        89
```

DNA RECOMBINATION IN EUKARYOTIC CELLS BY THE BACTERIOPHAGE PHIC31 RECOMBINATION SYSTEM

CROSS-REFERENCE TO RELATED APPLICATION

This application is a continuation of U.S. patent application Ser. No. 09/620,800, filed Jul. 21, 2000, which claims the benefit of U.S. Provisional Application No. 60/145,469, filed Jul. 23, 1999, which applications are incorporated herein by reference.

STATEMENT REGARDING FEDERALLY SPONSORED RESEARCH

This invention was made with government support under Grant No. 5335-21000-009-06S, awarded by the United States Department of Agriculture, Agricultural Research Service. The Government has certain rights in the invention.

BACKGROUND OF THE INVENTION

1. Field of the Invention

This invention pertains to the field of methods for obtaining specific and stable integration of nucleic acids into chromosomes of eukaryotes. The invention makes use of site-specific recombination systems that use prokaryotic recombinase polypeptides, such as the ΦC31 integrase.

2. Background

Genetic transformation of eukaryotes often suffers from significant shortcomings. For example, it is often difficult to reproducibly obtain integration of a transgene at a particular locus of interest. Homologous recombination generally occurs only at a very low frequency. To overcome this problem, site-specific recombination systems have been employed. These methods involve the use of site-specific recombination systems that can operate in higher eucaryotic cells.

Many bacteriophage and integrative plasmids encode site-specific recombination systems that enable the stable incorporation of their genome into those of their hosts. In these systems, the minimal requirements for the recombination reaction are a recombinase enzyme, or integrase, which catalyzes the recombination event, and two recombination sites (Sadowski (1986) *J. Bacteriol.* 165: 341-347; Sadowski (1993) *FASEB J.* 7: 760-767). For phage integration systems, these are referred to as attachment (att) sites, with an attP element from phage DNA and the attB element encoded by the bacterial genome. The two attachment sites can share as little sequence identity as a few base pairs. The recombinase protein binds to both att sites and catalyzes a conservative and reciprocal exchange of DNA strands that result in integration of the circular phage or plasmid DNA into host DNA. Additional phage or host factors, such as the DNA bending protein IHF, integration host factor, may be required for an efficient reaction (Friedman (1988) *Cell* 55:545-554; Finkel & Johnson (1992) *Mol. Microbiol.* 6: 3257-3265). The reverse excision reaction sometimes requires an additional phage factor, such as the xis gene product of phage λ (Weisberg & Landy (1983) "Site-specific recombination in phage lambda." In *Lambda II*, eds. Hendrix et al. (Cold Spring Harbor Laboratory, Cold Spring Harbor, N.Y.) pp. 211-250; Landy (1989) *Ann. Rev. Biochem.* 58: 913-949.

The recombinases have been categorized into two groups, the λ integrase (Argos et al. (1986) *EMBO J.* 5: 433-44; Voziyanov et al. (1999) *Nucl. Acids Res.* 27: 930-941) and the resolvase/invertase (Hatfull & Grindley (1988) "Resolvases and DNA-invertases: a family of enzymes active in site-specific recombination" In *Genetic Recombination*, eds. Kucherlipati, R., & Smith, G. R. (Am. Soc. Microbiol., Washington D.C.), pp. 357-396) families. These vary in the structure of the integrase enzymes and the molecular details of their mode of catalysis (Stark et al. (1992) *Trends Genetics* 8: 432-439). The temperate *Streptomyces* phage ΦC31 encodes a 68 kD recombinase of the latter class. The efficacy of the ΦC31 integrase enzyme in recombining its cognate attachment sites was recently demonstrated in vitro and in vivo in recA mutant *Escherichia coli* (Thorpe & Smith (1998) *Proc. Nat'l. Acad. Sci. USA* 95: 5505-5510). The ΦC31 integration reaction is simple in that it does not require a host factor and appears irreversible, most likely because an additional phage protein is required for excision. The phage and bacterial att sites share only three base pairs of homology at the point of cross-over. This homology is flanked by inverted repeats, presumably binding sites for the integrase protein. The minimal known functional size for both attB and attP is ~50 bp.

The Cre-lox system of bacteriophage P1, and the FLP-FRT system of *Saccharomyces cerevisiae* have been widely used for transgene and chromosome engineering in animals and plants (reviewed by Sauer (1994) *Curr. Opin. Biotechnol.* 5: 521-527; Ow (1996) *Curr. Opin. Biotechnol.* 7: 181-186). Other systems that operate in animal or plant cells include the following: 1) the R-RS system from *Zygosaccharomyces rouxii* (Onouchi et al. (1995) *Mol. Gen. Genet.* 247: 653-660), 2) the Gin-gix system from bacteriophage Mu (Maeser & Kahmann (1991) *Mol. Gen. Genet.* 230: 170-176) and, 3) the β recombinase-six system from bacterial plasmid pSM19035 (Diaz et al. (1999) *J. Biol. Chem.* 274: 6634-6640). By using the site-specific recombinases, one can obtain a greater frequency of integration.

However, these five systems suffer from a significant shortcoming. Each of these systems have in common the property that a single polypeptide recombinase catalyzes the recombination between two sites of identical or nearly identical sequences. The product-sites generated by recombination are themselves substrates for subsequent recombination. Consequently, recombination reactions are readily reversible. Since the kinetics of intramolecular interactions are favored over intermolecular interactions, these recombination systems are efficient for deleting rather than integrating DNA. Thus, a need exists for methods and systems for obtaining stable site-specific integration of transgenes. The present invention fulfills this and other needs.

SUMMARY OF THE INVENTION

The present invention provides methods for obtaining stable, site-specific recombination in a eukaryotic cell. Unlike previously known methods for site-specific recombination, the recombinants obtained using the methods of the invention are stable. The recombination reaction is not reversible.

The methods involve providing a eukaryotic cell that comprises a first recombination site and a second recombination site, which second recombination site can serve as a substrate for recombination with the first recombination site. The first and the second recombination sites are contacted with a prokaryotic recombinase polypeptide, resulting in recombination between the recombination sites, thereby forming one or two hybrid recombination sites. Significantly, the recombinase polypeptide is one that can mediate site-specific recombination between the first and second recombination sites, but cannot mediate recombination between the two hybrid recombination sites in the absence of an additional phage-produced factor that is not present in the eukaryotic cell. Either or both of the recombination sites can be present in a chromosome of the eukaryotic cell. In some embodiments, one of the recombination sites is present in the chromosome and the other is included within a nucleic acid that is to be integrated into the chromosome.

The invention also provides eukaryotic cells that contain a prokaryotic recombinase polypeptide or a nucleic acid that encodes a prokaryotic recombinase. In these embodiments, the recombinase is one that can mediate site-specific recombination between a first recombination site and a second recombination site that can serve as a substrate for recombination with the first recombination site, but in the absence of an additional factor that is not present in the eukaryotic cell cannot mediate recombination between two hybrid recombination sites that are formed upon recombination between the first recombination site and the second recombination site. In presently preferred embodiments, the cells of the invention include a nucleic acid that has a coding sequence for a recombinase polypeptide. The recombinase coding sequence is preferably operably linked to a promoter that mediates expression of the recombinase-encoding polynucleotide in the eukaryotic cell. The eukaryotic cells of the invention can be an animal cell, a plant cell, a yeast cell or a fungal cell, for example.

In additional embodiments, the invention provides methods for obtaining a eukaryotic cell having a stably integrated transgene. These methods involve introducing a nucleic acid into a eukaryotic cell that comprises a first recombination site, wherein the nucleic acid comprises the transgene of interest and a second recombination site which can serve as a substrate for recombination with the first recombination site. The first and second recombination sites are contacted with a prokaryotic recombinase polypeptide. The recombinase polypeptide catalyzes recombination between the first and second recombination sites, resulting in integration of the nucleic acid at the first recombination site, thereby forming a hybrid recombination site at each end of the nucleic acid. Again, the recombinase polypeptide is one that can mediate site-specific recombination between the first and second recombination sites, but cannot mediate recombination between two hybrid recombination sites in the absence of an additional factor that is not present in the eukaryotic cell.

Additional embodiments of the invention provide nucleic acids that include a polynucleotide sequence that encodes a bacterial recombinase polypeptide operably linked to a promoter that functions in a eukaryotic cell. The recombinase polypeptides encoded by these nucleic acids of the invention cannot mediate recombination between two hybrid recombination sites that are formed upon recombination between a first recombination site and a second recombination site in the absence of a bacteriophage factor that is not present in the eukaryotic cells. In some embodiments, the nucleic acids further include at least one recombination site that is recognized by the recombinase polypeptide.

Also provided by the invention are eukaryotic cells that include a polynucleotide that has one or more bacteriophage ΦC31 recombination sites, or recombination sites for other recombinases that cannot mediate recombination between two hybrid recombination sites that are formed upon recombination between a first recombination site and a second recombination site in the absence of a bacteriophage factor that is not present in the eukaryotic cells.

BRIEF DESCRIPTION OF THE DRAWINGS

FIG. 2 shows a schematic of an experiment which demonstrated that ΦC31 integrase catalyzes site-specific integration of a transgene encoding green fluorescent protein (GFP) in CHO cells.

FIG. 3 shows a schematic diagram of an experiment which demonstrated that ΦC31 catalyzes specific recombination at an attB site to insert a hygromycin phosphotransferase gene downstream of a chromosomally located promoter. Successful integration produces a Pc-attL-hpt linkage and a hygromycin resistance phenotype. The effect of different lengths of attP and attB sites were analyzed using the plasmids indicated.

DETAILED DESCRIPTION

Definitions

Figure 1:
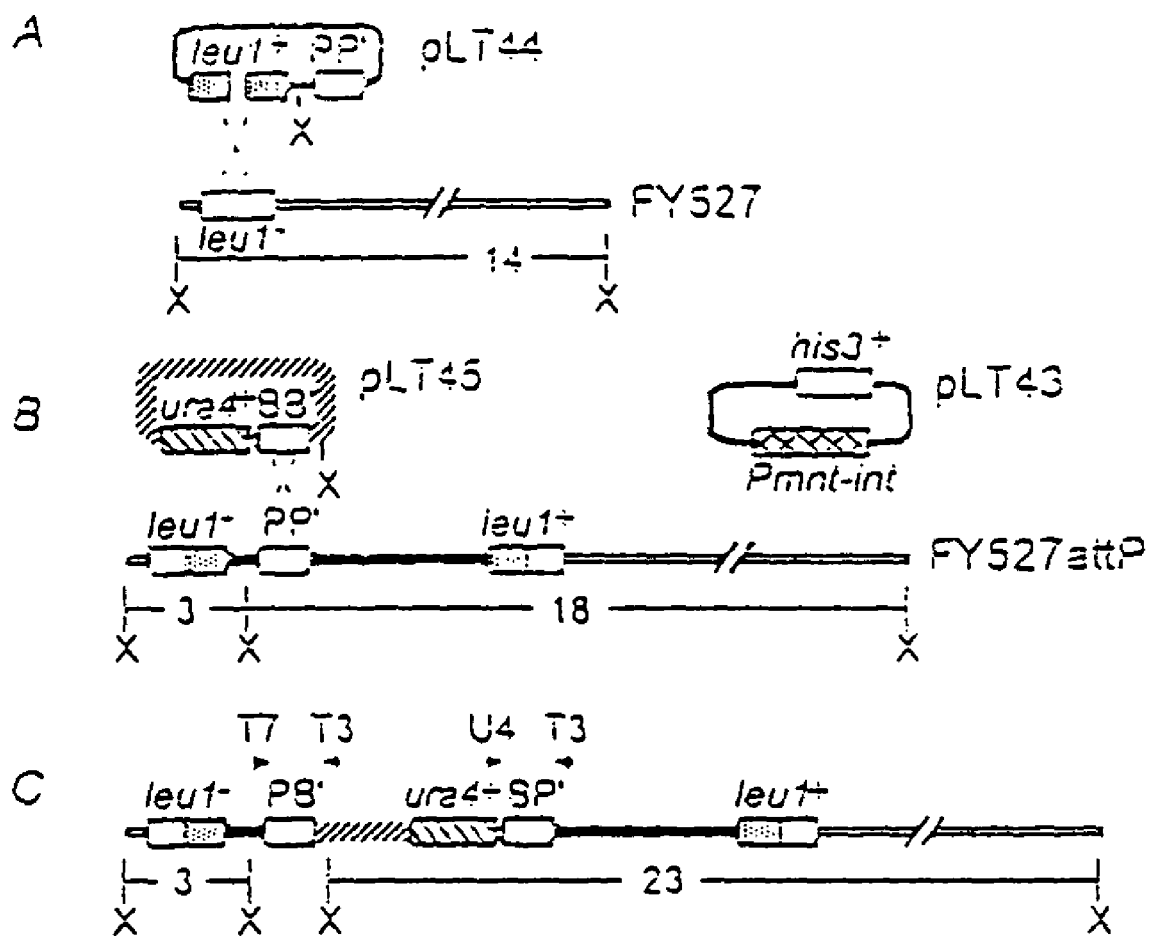
FIG. 1 shows a schematic (not to scale) representation of the chromosome structure at the S. pombe leu1 locus. Homologous insertion of pLT44 into the chromosome (FIG. 1A) places a ΦC31 attP target between leu1 alleles as shown in FIG. 1B. pLT43 promoted site-specific integration of pLT45 into the chromosomal attP target leads to the structure shown in FIG. 1C. Arrowheads indicate PCR primers corresponding to the T7 promoter (T7), T3 promoter (T3) and ura4$^+$ coding region (U4). Predicted sizes of XbaI (X) cleavage products are shown.

An "exogenous DNA segment", "heterologous polynucleotide" a "transgene" or a "heterologous nucleic acid", as used herein, is one that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605-2608; Cassol et al. (1992); Rossolini et al. (1994) *Mol. Cell. Probes* 8: 91-98). The term nucleic acid is used interchangeably with gene, cDNA, and mRNA encoded by a gene.

"Nucleic acid derived from a gene" refers to a nucleic acid for whose synthesis a gene, or a subsequence thereof (e.g., coding region), has ultimately served as a template. Thus, an mRNA, a cDNA reverse transcribed from an mRNA, an RNA transcribed from that cDNA, a DNA amplified from the cDNA, an RNA transcribed from the amplified DNA, etc., are all derived from the gene and detection of such derived products is indicative of the presence and/or abundance of the original.

A DNA segment is "operably linked" when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers, for example, need not be contiguous with the coding sequences whose transcription they control. Linking is accomplished by ligation at convenient restriction sites or at adapters or linkers inserted in lieu thereof.

"Plant" includes whole plants, plant organs (e.g., leaves, stems, roots, etc.), seeds and plant cells and progeny of same. The class of plants that can be used in the methods of the invention is generally as broad as the class of higher plants amenable to transformation techniques, including both monocotyledonous and dicotyledonous plants.

"Promoter" refers to a region of DNA involved in binding the RNA polymerase to initiate transcription. An "inducible promoter" refers to a promoter that directs expression of a gene where the level of expression is alterable by environmental or developmental factors such as, for example, temperature, pH, transcription factors and chemicals.

The term "recombinant" when used with reference to a cell indicates that the cell replicates a heterologous nucleic acid, or expresses a peptide or protein encoded by a heterologous nucleic acid. Recombinant cells can contain polynucleotides that are not found within the native (non-recombinant) form of the cell. Recombinant cells can also contain polynucleotides found in the native form of the cell wherein the polynucleotides are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

"Recombinase" refers to an enzyme that catalyzes recombination between two or more recombination sites. Recombinases useful in the present invention catalyze recombination at specific recombination sites which are specific polynucleotide sequences that are recognized by a particular recombinase. The term "integrase" refers to a type of recombinase.

"transformation rate" refers to the percent of cells that successfully incorporate a heterologous polynucleotide into its genome and survive.

The term "transgenic" refers to a cell that includes a specific modification that was introduced into the cell, or into an ancestor of the cell. Such modifications can include one or more point mutations, deletions, insertions, or combinations thereof. When referring to an animal, the term "transgenic" means that the animal includes cells that are transgenic. An animal that is composed of both transgenic and non-transgenic cells is referred to herein as a "chimeric" animal.

The term "vector" refers to a composition for transferring a nucleic acid (or nucleic acids) to a host cell. A vector comprises a nucleic acid encoding the nucleic acid to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

"Recombination sites" are specific polynucleotide sequences that are recognized by the recombinase enzymes described herein. Typically, two different sites are involved (termed "complementary sites"), one present in the target nucleic acid (e.g., a chromosome or episome of a eukaryote) and another on the nucleic acid that is to be integrated at the target recombination site. The terms "attB" and "attP," which refer to attachment (or recombination) sites originally from a bacterial target and a phage donor, respectively, are used herein although recombination sites for particular enzymes may have different names. The recombination sites typically include left and right arms separated by a core or spacer region. Thus, an attB recombination site consists of BOB', where B and B' are the left and right arms, respectively, and O is the core region. Similarly, attP is POP', where P and P' are the arms and O is again the core region. Upon recombination between the attB and attP sites, and concomitant integration of a nucleic acid at the target, the recombination sites that flank the integrated DNA are referred to as "attL" and "aatR." The attL and attR sites, using the terminology above, thus consist of BOP' and POB', respectively. In some representations herein, the "O" is omitted and attB and attP, for example, are designated as BB' and PP', respectively.

DESCRIPTION OF THE PREFERRED EMBODIMENTS

The present invention provides methods for obtaining site-specific recombination in eukaryotic cells. Unlike previously known systems for obtaining site-specific recombination, the products of the recombinations performed using the methods of the invention are stable. Thus, one can use the methods to, for example, introduce transgenes into chromosomes of eukaryotic cells and avoid the excision of the transgene that often occurs using previously known site-specific recombination systems. Stable inversions, translocations, and other rearrangements can also be obtained.

The invention employs prokaryotic recombinases, such as bacteriophage integrases, that are unidirectional in that they can catalyze recombination between two complementary recombination sites, but cannot catalyze recombination between the hybrid sites that are formed by this recombination. One such recombinase, the ΦC31 integrase, by itself catalyzes only the attB×attP reaction. The integrase cannot mediate recombination between the attL and attR sites that are formed upon recombination between attB and attP. Because recombinases such as the ΦC31 integrase cannot alone catalyze the reverse reaction, the ΦC31 attB×attP recombination is stable. This property is one that sets the methods of the present invention apart from site-specific recombination systems currently in use for eucaryotic cells, such as the Cre-lox or FLP-FRT system, where the recombination reactions can readily reverse. Use of the recombination systems of the invention provides new opportunities for directing stable transgene and chromosome rearrangements in eukaryotic cells.

The methods involve contacting a pair of recombination sites (e.g., attB and attP) that are present in a eukaryotic cell with a corresponding recombinase. The recombinase then mediates recombination between the recombination sites. Depending upon the relative locations of the two recombination sites, any one of a number of events can occur as a result of the recombination. For example, if the two recombination sites are present on different nucleic acid molecules, the recombination can result in integration of one nucleic acid molecule into a second molecule. Thus, one can obtain integration of a plasmid that contains one recombination site into a eukaryotic cell chromosome that includes the corresponding recombination site. Because the recombinases used in the methods of the invention cannot catalyze the reverse reaction, the integration is stable. Such methods are useful, for example, for obtaining stable integration into the eukaryotic chromosome of a transgene that is present on the plasmid.

The two recombination sites can also be present on the same nucleic acid molecule. In such cases, the resulting product typically depends upon the relative orientation of the sites. For example, recombination between sites that are in the direct orientation will generally result in excision of any DNA that lies between the two recombination sites. In contrast, recombination between sites that are in the reverse orientation can result in inversion of the intervening DNA. Again, the resulting rearranged nucleic acid is stable in that the recombination is irreversible in the absence of an additional factor, generally encoded by the particular bacteriophage from which the recombinase is derived, that is not normally found in eukaryotic cells. One example of an application for which this method is useful involves the placement of a promoter between the two recombination sites. If the promoter is initially in the opposite orientation relative to a coding sequence that is to be expressed by the promoter and the recombination sites that flank the promoter are in the inverted orientation, contacting the recombination sites will result in inversion of the promoter, thus placing the promoter in the correct orientation to drive expression of the coding sequence. Similarly, if the promoter is initially in the correct orientation for expression and the recombination sites are in the same orientation, contacting the recombination sites with the promoter can result in excision of the promoter fragment, thus stopping expression of the coding sequence.

The methods of the invention are also useful for obtaining translocations of chromosomes, for example. In these embodiments, one recombination site is placed on one chromosome and a second recombination site that can serve as a substrate for recombination with the first recombination site is placed on a second chromosome. Upon contacting the two recombination sites with a recombinase, recombination occurs that results in swapping of the two chromosome arms. For example, one can construct two strains of an organism, one strain of which includes the first recombination site and the second strain that contains the second recombination site. The two strains are then crossed, to obtain a progeny strain that includes both of the recombination sites. Upon contacting the sites with the recombinase, chromosome arm swapping occurs.

Recombinases and Recombination Sites

The methods of the invention use recombinase systems to achieve stable integration or other rearrangement of nucleic acids in eukaryotic cells. A recombinase system typically consists of three elements: two specific DNA sequences ("the recombination sites") and a specific enzyme ("the recombinase"). The recombinase catalyzes a recombination reaction between the specific recombination sites.

Recombination sites have an orientation. In other words, they are not palindromes. The orientation of the recombination sites in relation to each other determines what recombination event takes place. The recombination sites may be in two different orientations: parallel (same direction) or opposite. When the recombination sites are present on a single nucleic acid molecule and are in a parallel orientation to each other, then the recombination event catalyzed by the recombinase is a typically an excision of the intervening nucleic acid, leaving a single recombination site. When the recombination sites are in the opposite orientation, then any intervening sequence is typically inverted.

The recombinases used in the methods of the invention can mediate site-specific recombination between a first recombination site and a second recombination site that can serve as a substrate for recombination with the first recombination site. However, in the absence of an additional factor that is not normally present in eukaryotic cells, cannot mediate recombination between two hybrid recombination sites that are formed upon recombination between the first recombination site and the second recombination site. Examples of these recombinases include, for example, the bacteriophage ΦC31 integrase (see, e.g., Thorpe & Smith (1998) *Proc. Nat'l. Acad. Sci. USA* 95: 5505-5510; Kuhstoss & Rao (1991) *J. Mol. Biol.* 222: 897-890; U.S. Pat. No. 5,190,871), a phage P4 recombinase (Ow & Ausubel (1983) *J. Bacteriol.* 155: 704-713), a *Listeria* phage recombinase, a bacteriophage R4 Sre recombinase (Matsuura et al. (1996) *J. Bacteriol.* 178: 3374-3376), a CisA recombinase (Sato et al. (1990) *J. Bacteriol.* 172: 1092-1098; Stragier et al. (1989) *Science* 243: 507-512), an XisF recombinase (Carrasco et al. (1994) *Genes Dev.* 8: 74-83), and a transposon Tn4451 TnpX recombinase (Bannam et al. (1995) *Mol. Microbiol.* 16: 535-551; Crelin & Rood (1997) *J. Bacteriol.* 179: 5148-5156).

Recombinase polypeptides, and nucleic acids that encode the recombinase polypeptides, are described in the art and can be obtained using routine methods. For example, a vector that includes a nucleic acid fragment that encodes the ΦC31 integrase is described in U.S. Pat. No. 5,190,871 and is available from the Northern Regional Research Laboratories, Peoria, Ill. 61604) under the accession number B-18477.

The recombinases can be introduced into the eukaryotic cells that contain the recombination sites at which recombination is desired by any suitable method. For example, one can introduce the recombinase in polypeptide form, e.g., by microinjection or other methods. In presently preferred embodiments, however, a gene that encodes the recombinase is introduced into the cells. Expression of the gene results in production of the recombinase, which then catalyzes recombination among the corresponding recombination sites. One can introduce the recombinase gene into the cell before, after, or simultaneously with, the introduction of the exogenous polynucleotide of interest. In one embodiment, the recombinase gene is present within the vector that carries the polynucleotide that is to be inserted; the recombinase gene can even be included within the polynucleotide. In other embodiments, the recombinase gene is introduced into a transgenic eukaryotic organism, e.g., a transgenic plant, animal, fungus, or the like, which is then crossed with an organism that contains the corresponding recombination sites.

Target Organisms

The methods of the invention are useful for obtaining stable integration and/or rearrangement of DNA in any type of eukaryotic cell. For example, the methods are useful for cells of animals, plants, fungi, bacteria and other microorganisms. In some embodiments, the cells are part of a multicellular organism, e.g., a transgenic plant or animal. The methods of the invention are particularly useful in situations where transgenic materials are difficult to obtain, such as with transgenic wheat, corn, and animals. In these situations, finding the rare single copy insertion requires the prior attainment of a large number of independently derived transgenic clones, which itself requires great expenditure of effort.

Among the plant targets of particular interest are monocots, including, for example, rice, corn, wheat, rye, barley, bananas, palms, lilies, orchids, and sedges. Dicots are also suitable targets, including, for example, tobacco, apples, potatoes, beets, carrots, willows, elms, maples, roses, buttercups, petunias, phloxes, violets and sunflowers. Other targets include animal and fungal cells. These lists are merely illustrative and not limiting.

Constructs for Introduction of Exogenous DNA into Target Cells

The methods of the invention often involve the introduction of exogenous DNA into target cells. For example, nucleic acids that include one or more recombination sites are often introduced into the cells. The polynucleotide constructs that are to be introduced into the cells can include, in addition to the recombination site or sites, a gene or other functional sequence that will confer a desired phenotype on the cell.

In some embodiments, a polynucleotide construct that encodes a recombinase is introduced into the eukaryotic cells in addition to the recombination sites. The recombinase-encoding polypeptide can be included on the same nucleic acid as the recombination site or sites, or can be introduced into the cell as a separate nucleic acid. The present invention provides nucleic acids that include recombination sites, as well as nucleic acids in which a recombinase-encoding polynucleotide sequence is operably linked to a promoter that functions in the target eukaryotic cell.

Generally, a polynucleotide that is to be expressed (e.g., a recombinase-encoding polynucleotide or transgene of interest) will be present in an expression cassette, meaning that the polynucleotide is operably linked to expression control signals, e.g., promoters and terminators, that are functional in the host cell of interest. The genes that encode the recombinase and the selectable marker, will also be under the control of such signals that are functional in the host cell. Control of expression is most easily achieved by selection of a promoter. The transcription terminator is not generally as critical and a variety of known elements may be used so long as they are recognized by the cell.

A promoter can be derived from a gene that is under investigation, or can be a heterologous promoter that is obtained from a different gene, or from a different species. Where direct expression of a gene in all tissues of a transgenic plant or other organism is desired, one can use a "constitutive" promoter, which is generally active under most environmental conditions and states of development or cell differentiation. Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, *Arabidopsis* (Sun and Callis, *Plant J.*, 11(5):1017-1027 (1997)), the mas, Mac or DoubleMac promoters (described in U.S. Pat. No. 5,106,739 and by Comai et al., *Plant Mol. Biol.* 15:373-381 (1990)) and other transcription initiation regions from various plant genes known to those of skill in the art. Such genes include for example, ACT11 from *Arabidopsis* (Huang et al., *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al., *Plant Physiol.* 104:1167-1176 (1994)), GPc1 from maize (GenBank No. X15596, Martinez et al., *J. Mol. Biol* 208:551-565 (1989)), and Gpc2 from maize (GenBank No. U45855, Manjunath et al., *Plant Mol. Biol.* 33:97-112 (1997)). Useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the α-conglycinin promoter, the phaseolin promoter, the ADH promoter, and heat-shock promoters.

Promoters for use in *E. coli* include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1-10 (Johnson and Davies (1984) *Mol. Cell. Biol.* 4:1440-1448) ADH2 (Russell et al. (1983) *J. Biol. Chem.* 258:2674-2682), PHO5 (*EMBO J.* (1982) 6:675-680), and MFα (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181-209).

Alternatively, one can use a promoter that directs expression of a gene of interest in a specific tissue or is otherwise under more precise environmental or developmental control. Such promoters are referred to here as "inducible" or "repressible" promoters. Examples of environmental conditions that may effect transcription by inducible promoters include pathogen attack, anaerobic conditions, ethylene or the presence of light. Promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations. Inducible promoters are often used to control expression of the recombinase gene, thus allowing one to control the timing of the recombination reaction. Examples of tissue-specific plant promoters under developmental control include promoters that initiate transcription only in certain tissues, such as fruit, seeds, or flowers. The tissue-specific E8 promoter from tomato is particularly useful for directing gene expression so that a desired gene product is located in fruits. See, e.g., Lincoln et al. (1988) *Proc. Nat'l. Acad. Sci. USA* 84: 2793-2797; Deikman et al. (1988) *EMBO J.* 7: 3315-3320; Deikman et al. (1992) *Plant Physiol.* 100: 2013-2017. Other suitable promoters include those from genes encoding embryonic storage proteins. Examples of environmental conditions that may affect transcription by inducible promoters include anaerobic conditions, elevated temperature, or the presence of light. Additional organ-specific, tissue-specific and/or inducible foreign promoters are also known (see, e.g., references cited in Kuhlemeier et al (1987) *Ann. Rev. Plant Physiol.* 38:221), including those 1,5-ribulose bisphosphate carboxylase small subunit genes of *Arabidopsis thaliana* (the "ssu" promoter), which are light-inducible and active only in photosynthetic tissue, anther-specific promoters (EP 344029), and seed-specific promoters of, for example, *Arabidopsis thaliana* (Krebbers et al. (1988) *Plant Physiol.* 87:859). Exemplary green tissue-specific promoters include the maize phosphoenol pyruvate carboxylase (PEPC) promoter, small submit ribulose bis-carboxylase promoters (ss-RUBISCO) and the chlorophyll a/b binding protein promoters. The promoter may also be a pith-specific promoter, such as the promoter isolated from a plant TrpA gene as described in International Publication No. WO93/07278.

Inducible promoters for other organisms include, for example, the arabinose promoter, the lacZ promoter, the metallothionein promoter, and the heat shock promoter, as well as many others that are known to those of skill in the art. An example of a repressible promoter useful in yeasts such as *S. pombe* is the Pmnt promoter, which is repressible by vitamin B1.

Typically, constructs to be introduced into these cells are prepared using recombinant expression techniques. Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, used to transfect cells or incorporated into *Agrobacterium tumefaciens* to infect and transform plants. Where *Agrobacterium* is the means of transformation, shuttle vectors are constructed. Cloning in *Streptomyces* or *Bacillus* is also possible.

Selectable markers are often incorporated into the polynucleotide constructs and/or into the vectors that are used to introduce the constructs into the target cells. These markers permit the selection of colonies of cells containing the polynucleotide of interest. Often, the vector will have one selectable marker that is functional in, e.g., *E. coli*, or other cells in which the vector is replicated prior to being introduced into the target cell. Examples of selectable markers for *E. coli* include: genes specifying resistance to antibiotics, i.e., ampicillin, tetracycline, kanamycin, erythromycin, or genes conferring other types of selectable enzymatic activities such as β-galactosidase, or the lactose operon. Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) *Proc. Nat'l. Acad. Sci. USA* 78: 2072; Southern & Berg (1982) *J. Mol. Appl. Genet.* 1: 327).

Selection markers for plant cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg (hpt) gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

If more than one exogenous nucleic acid is to be introduced into a target eukaryotic cell, it is generally desirable to use a different selectable marker on each exogenous nucleic acid. This allows one to simultaneously select for cells that contain both of the desired exogenous nucleic acids.

Methods for Introducing Constructs into Target Cells

The polynucleotide constructs that include recombination sites and/or recombinase-encoding genes can be introduced into the target cells and/or organisms by any of the several means known to those of skill in the art. For instance, the DNA constructs can be introduced into plant cells, either in culture or in the organs of a plant by a variety of conventional techniques. For example, the DNA constructs can be introduced directly to plant cells using biolistic methods, such as DNA particle bombardment, or the DNA construct can be introduced using techniques such as electroporation and microinjection of plant cell protoplasts. Particle-mediated transformation techniques (also known as "biolistics") are described in Klein et al., *Nature,* 327:70-73 (1987); Vasil, V. et al., *Bio/Technol.* 11:1553-1558 (1993); and Becker, D. et al., *Plant J.,* 5:299-307 (1994). These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants, bacteria, fungi, algae, intact animal tissues, tissue culture cells, and animal embryos. One can employ electronic pulse delivery, which is essentially a mild electroporation format for live tissues in animals and patients. Zhao, *Advanced Drug Delivery Reviews* 17:257-262 (1995).

Other transformation methods are also known to those of skill in the art. Microinjection techniques are known in the art and well described in the scientific and patent literature. The introduction of DNA constructs using polyethylene glycol (PEG) precipitation is described in Paszkowski et al., *EMBO J.* 3:2717 (1984). Electroporation techniques are described in Fromm et al., *Proc. Natl. Acad. Sci. USA,* 82:5824 (1985). PEG-mediated transformation and electroporation of plant protoplasts are also discussed in Lazzeri, P., *Methods Mol. Biol.* 49:95-106 (1995). Methods are known for introduction and expression of heterologous genes in both monocot and dicot plants. See, e.g., U.S. Pat. Nos. 5,633,446, 5,317,096, 5,689,052, 5,159,135, and 5,679,558; Weising et al. (1988) *Ann. Rev. Genet.* 22:421-477. Transformation of monocots in particular can use various techniques including electroporation (e.g., Shimamoto et al., *Nature* (1992), 338:274-276); biolistics (e.g., European Patent Application 270,356); and *Agrobacterium* (e.g., Bytebier et al., *Proc. Nat'l Acad. Sci. USA* (1987) 84:5345-5349).

For transformation of plants, DNA constructs may be combined with suitable T-DNA flanking regions and introduced into a conventional *Agrobacterium tumefaciens* host vector. The virulence functions of the *A. tumefaciens* host will direct the insertion of a transgene and adjacent marker gene(s) (if present) into the plant cell DNA when the cell is infected by the bacteria. *Agrobacterium tumefaciens*—meditated transformation techniques are well described in the scientific literature. See, for example, Horsch et al. *Science,* 233:496-498 (1984), Fraley et al., *Proc. Natl. Acad. Sci. USA,* 80:4803 (1983), and Hooykaas, *Plant Mol. Biol.,* 13:327-336 (1989), Bechtold et al., *Comptes Rendus De L Academie Des Sciences Serie Iii-Sciences De La Vie-Life Sciences,* 316:1194-1199 (1993), Valvekens et al., *Proc. Natl. Acad. Sci. USA,* 85:5536-5540 (1988). For a review of gene transfer methods for plant and cell cultures, see, Fisk et al., *Scientia Horticulturae* 55:5-36 (1993) and Potrykus, *CIBA Found. Symp.* 154:198 (1990).

Other methods for delivery of polynucleotide sequences into cells include, for example liposome-based gene delivery (Debs and Zhu (1993) WO 93/24640; Mannino and Gould-Fogerite (1988) *BioTechniques* 6(7): 682-691; Rose U.S. Pat. No. 5,279,833; Brigham (1991) WO 91/06309; and Felgner et al. (1987) *Proc. Natl. Acad. Sci. USA* 84: 7413-7414), as well as use of viral vectors (e.g., adenoviral (see, e.g., Berns et al. (1995) *Ann. NY Acad. Sci.* 772: 95-104; Ali et al. (1994) *Gene Ther.* 1: 367-384; and Haddada et al. (1995) *Curr. Top. Microbiol. Immunol.* 199 (Pt 3): 297-306 for review), papillomaviral, retroviral (see, e.g., Buchscher et al. (1992) *J. Virol.* 66(5) 2731-2739; Johann et al. (1992) *J. Virol.* 66 (5):1635-1640 (1992); Sommerfelt et al., (1990) *Virol.* 176: 58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology, Third Edition* Paul (ed) Raven Press, Ltd., New York and the references therein, and Yu et al., *Gene Therapy* (1994) supra.), and adeno-associated viral vectors (see, West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invst.* 94:1351 and Samulski (supra) for an overview of AAV vectors; see also, Lebkowski, U.S. Pat. No. 5,173,414; Tratschin et al. (1985) *Mol. Cell. Biol.* 5(11):3251-3260; Tratschin et al. (1984) *Mol. Cell. Biol.,* 4:2072-2081; Hermonat and Muzyczka (1984) *Proc. Natl. Acad. Sci. USA,* 81:6466-6470; McLaughlin et al. (1988) and Samulski et al. (1989) *J. Virol.,* 63:03822-3828), and the like.

Methods by which one can analyze the integration pattern of the introduced exogenous DNA are well known to those of skill in the art. For example, one can extract DNA from the transformed cells, digest the DNA with one or more restriction enzymes, and hybridize to a labeled fragment of the polynucleotide construct. The inserted sequence can also be identified using the polymerase chain reaction (PCR). See, e.g., Sambrook et al., *Molecular Cloning—A Laboratory Manual,* Cold Spring Harbor Laboratory, Cold Spring Harbor, N.Y., 1989 for descriptions of these and other suitable methods.

Regeneration of Transgenic Plants and Animals

The methods of the invention are particularly useful for obtaining transgenic and chimeric multicellular organisms that have a stably integrated exogenous polynucleotide or other stable rearrangement of cellular nucleic acids. Methods for obtaining transgenic and chimeric organisms, both plants and animals, are well known to those of skill in the art.

Transformed plant cells, derived by any of the above transformation techniques, can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., *Protoplasts Isolation and Culture, Handbook of Plant Cell Culture,* pp. 124-176, Macmillian Publishing Company, New York (1983); and in Binding, *Regeneration of Plants, Plant Protoplasts,* pp. 21-73, CRC Press, Boca Raton, (1985). Regeneration can also be obtained from plant callus, explants, somatic embryos (Dandekar et al., *J. Tissue Cult. Meth.,* 12:145 (1989); McGranahan et al., *Plant Cell Rep.,* 8:512 (1990)), organs, or parts thereof. Such regeneration techniques are described generally in Klee et al., *Ann. Rev. of Plant Phys.,* 38:467-486 (1987).

The methods are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals,* VCH Publ., 1993; Murphy and Carter, Eds., *Transgenesis Techniques: Principles and Protocols* (*Methods in Molecular Biology*, Vol. 18), 1993; and Pinkert, C A., Ed., *Transgenic Animal Technology: A Laboratory Handbook*, Academic Press, 1994. Transgenic fish having specific genetic modifications can also be made using the claimed methods. See, e.g., Iyengar et al. (1996) *Transgenic Res.* 5: 147-166 for general methods of making transgenic fish.

One method of obtaining a transgenic or chimeric animal having specific modifications in its genome is to contact fertilized oocytes with a vector that includes the polynucleotide of interest flanked by recombination sites. For some animals, such as mice fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16-150 cells. The 16-32 cell stage of an embryo is described as a morula. Pre-implantation embryos containing more than 32 cells are termed blastocysts. These embryos show the development of a blastocoel cavity, typically at the 64 cell stage. If desired, the presence of a desired exogenous polynucleotide in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual*, C. S. H. L. N.Y. (1986) (mouse embryo); Hammer et al. (1985) *Nature* 315: 680 (rabbit and porcine embryos); Gandolfi et al. (1987) *J. Reprod. Fert.* 81: 23-28; Rexroad et al. (1988) *J. Anim. Sci.* 66: 947-953 (ovine embryos) and Eyestone et al. (1989) *J. Reprod. Fert.* 85: 715-720; Camous et al. (1984) *J. Reprod. Fert.* 72: 779-785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the methods can be used to obtain embryonic stem cells (ES) that have a single copy of the desired exogenous polynucleotide. These cells are obtained from preimplantation embryos cultured in vitro. See, e.g., Hooper, ML, *Embryonal Stem Cells: Introducing Planned Changes into the Animal Germline* (Modern Genetics, v. 1), Int'l. Pub. Distrib., Inc., 1993; Bradley et al. (1984) *Nature* 309, 255-258. Transformed ES cells are combined with blastocysts from a non-human animal. The ES cells colonize the embryo and in some embryos form the germ line of the resulting chimeric animal. See Jaenisch, *Science*, 240: 1468-1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810-813.

EXAMPLES

The following examples are offered to illustrate, but not to limit the present invention.

Example 1

The ΦC31 Recombination System Functions in *Schizosaccharomyces pombe*

This Example demonstrates that the *Streptomyces* bacteriophage ΦC31 site-specific recombination system functions in eukaryotic cells. A bacteriophage attachment site (attP) was introduced into a chromosome of *Schizosaccharomyces pombe* at the *S. pombe* leu1 locus. This target strain was subsequently transformed with a plasmid that contains the bacterial attachment site (attB) linked to a ura4$^+$ selectable marker. When co-transformed with a second plasmid harboring the ΦC31 integrase gene, high efficiency transformation to Ura$^+$ was observed under conditions where the integrase gene was expressed.

Southern analysis of the integration events shows insertion of the attB-ura4$^+$ plasmid into the attP site of the leu1 locus. Nucleotide sequence of the hybrid junctions revealed that the attB×attP recombination reaction is precise.

Materials and Methods

Recombinant DNA

Standard methods were used throughout. *E. coli* strain XL2-Blue (recA1 endA1 gyrA96 thi-1 hsdR17 supE44 relA1 lac [F' proAB lacI$^q$ZΔM15Tn10 (Tet$^r$) Amy Cam$^r$], Stratagene) served as host for DNA constructs.

Media

Fission yeast strains were grown on minimal medium (EMM-low glucose, from Bio101) supplemented as needed with 225 mg/l adenine, histidine, leucine or uracil. Minimal plates with 5-FOA (5-floroorotic acid, from Zymo Research, Inc.) were prepared according to Grimm et al. ((1988) *Mol. Gen. Genet.* 215: 81-86) and were supplemented with adenine, histidine, and leucine. When used, thiamine was added to 5 µg/ml.

*S. pombe* with Φ31 attP Target

The 84 bp ΦC31 attP site (abbreviated as PP'), isolated as an ApaI-SacI fragment from pHS282 (Thorpe & Smith (1998) *Proc. Nat'l. Acad. Sci. USA* 95:5505-5510) was cloned into the same sites of the *S. pombe* integrating vector pJK148 (Keeney & Boeke (1994) *Genetics* 136:849-856) to make pLT44. This plasmid was targeted to the *S. pombe* leu1-32 allele by lithium acetate mediated transformation with NdeI cut DNA. The recipient host FY527 (h$^-$ ade6-M216 his3-D1 leu1-32 ura4-D18), converted to Leu$^+$ by homologous recombination with pLT44, was examined by Southern analysis. One Leu$^+$ transformant, designated FY527attP, was found to contain a single copy of pLT44. Another transformant, designated FY527attPx2, harbors a tandem plasmid insertion.

Integrative ura4$^+$ Vector with ϕC31 attB Site

The *S. pombe* ura4$^+$ gene, excised from pTZura4 (S. Forsburg) on a 1.8 kb EcoRI-BamHI fragment, was inserted into pJK148 cut with the same enzymes to create pLT40. The ΦC31 attB site (abbreviated as BB'), isolated from pHS21 as a 500 bp BamHI-XbaI fragment, was ligated into pLT40 cut with those enzymes, creating pLT42. Most of the leu1 gene was removed from pLT42 by deleting a XhoI fragment to create pLT45. This removed all but 229 bp of leu1 from pLT45 and reduced its transformation efficiency to that of a plasmid without any leu1 homology. pLT50, which has a second attB site in the same orientation immediately on the other side of ura4, was constructed by first subcloning the attB BamHI-SacI fragment from pLT42 into pUC19, excising it with EcoRI and SalII, and subsequently inserting it into pLT45 cut with EcoRI and XhoI. The second attB site in the final construct was sequenced once on each strand and found to be identical to the first attB site.

Linear DNA Transformation

The attB-ura4⁺-attB linear DNA was prepared as an AttII-AlwNI fragment purified from pLT50, or as a PCR product using pLT50 as template. PCR was conducted using standard conditions with a T3 primer and a second primer (5' ggc cct gaa att gtt gct tct gcc 3') corresponding to the plasmid backbone of pJK148.

Repressible Synthesis of ΦC31 Integrase

The *S. pombe* Pmnt promoter, repressible by vitamin B1, was excised as a 1.2 kb PstI-SacI fragment from pMO147 and inserted into the his3⁺, ars1 vector pBG2 (Ohi et al. (1996) *Gene* 174: 315-318) cut with the same enzymes, creating pLT41. A 2.0 kb SacI fragment containing the ΦC31 int coding region was transferred from pHS33 (Thorpe & Smith (1998) supra.) to the SacI site of pLT41. A clone in which the int coding region is oriented such that expression is under the control of Pmnt was designated pLT43.

Molecular Analyses

Southern analysis was performed using the Genius™ system from Boehringer Mannheim. A 998 bp internal EcoRV fragment of leu1, a 1.8 kb fragment of ura4, and the 2.0 kb ΦC31 int gene were digoxigen-labeled by the random primer method and used as probes. Polymerase chain reaction was performed on a Perkin Elmer Cetus Gene Amp PCR 9600 using Stratagene Turbo PFU enzyme or VENT polymerase. The standard T3 and T7 primers were used where possible. The ura4 primer (5' gtc aaa aag ttt cgt caa tat cac 3' (SEQ ID NO: 1)) and the pJK148 primers were purchased from Operon Technologies. For all PCR reactions an annealing temperature of 51° C. and a 30-second extension time were used.

Results and Discussion

Inserting a Target Site into the *S. pombe* Genome

To create a host strain with a target site for ΦC31-mediated integration, the ΦC31 attP site was inserted by homologous recombination into the leu1 locus of the fission yeast genome to form the Leu⁺ strain FY527attP (FIG. 1A). Previous studies showed that when *S. pombe* DNA is cleaved with XbaI and probed with an internal 1 kb fragment of the leu1⁺ gene, the probe detects a 14 kb band (Keeney & Boeke (1994) *Genetics* 136: 849-856). Insertion of the leu⁺ plasmid pJK148 at the leu1-32 locus results in detection of 3 and 18 kb bands (FIG. 1A). Since pLT44 differs from pJK148 by the inclusion of an 84 bp ΦC31 attP element, integration of pLT44 at leu1-32 yielded the same 3 kb and 18 kb hybridization pattern in FY527attP. The absence of other hybridizing fragments indicates that the pLT44 DNA resides as a single integrated copy.

ΦC31-Integase-Mediated Transformation

FY527atttP was transformed with pLT45, which harbors ura4⁺ and an attB sequence (BB') but lacks an origin of replication. This construct was introduced by itself or with pLT43, a his3⁺ replicating vector that produces ΦC31 integrase. The inclusion of pLT43 increased the number of Ura⁺ transformants an average of 15 fold (Table 1). This enhancement cannot be attributed to the recombination between pLT45 and the replication-proficient pLT43, as its effect is dependent on integrase gene expression. Transcription of the integrase gene is under the control of Pmnt, a promoter repressible by high levels of vitamin B1 (Maundrell, K. (1993) *Gene* 123: 127-130). The repression is not absolute (Forsburg, S. L. (1993) *Nucleic Acids Res* 21: 2955-2956) but reduces the production of integrase protein. When thiamine was added to the growth medium, the number of Ura⁺ transformants decreased to near background level. The frequency of Ura⁺ tranformants did not change significantly whether or not the integrase plasmid was co-selected by omission of histidine from the medium. The transformation competency of FY527attP was estimated from the number of His⁺ transformants obtained with pLT43 or its progenitor plasmid pBG2. Compared to the frequency of either replicating plasmid, the pLT43-dependent transformation of FY527attP averaged about 15%.

TABLE 1

Integrase-dependent site-specific insertion in *S. pombe* FY527attP.

| DNA (1 μg) | Selection | B1 (5 μg) | Transformants per 10⁷ cells (±sd)* | Relative Value§ | Class a | Class b | Others |
|---|---|---|---|---|---|---|---|
| pLT43 | His⁺ | − | 7200 (±2200) | 100 | | | |
| pLT45 | Ura⁺ | − | 63 (±10) | 1 | 0%‡ | 0%‡ | 100%‡ |
| pLT45 + pLT43 | Ura⁺ | − | 1100 (±120) | 15 | 88%† | 6%† | 6%† |
| pLT45 + pLT43 | Ura⁺ | + | 120 (±16) | 2 | 0%‡ | 25%‡ | 75%‡ |

*From three independent experiments
§(transformation efficiency of the DNA of intrest)/(transformation efficiency of pLT43) × 100
†n = 16
‡n = 8

ΦC31-Integrase Promoted attPxattB Recombination

Recombination between the pLT45-encoded ΦC31 attB element and the chromosomally situated attP sequence would incorporate the circular DNA into the leu1 locus as depicted in FIG. 1B. If this reaction occurs, XbaI-fractionated genomic DNA from the Ura⁺ transformants is probed with leu1 DNA, the 3 kb band will remain unchanged, while the 18 kb band will increase to ~23 kb (FIG. 1C). Randomly selected Ura⁺ colonies were examined by hybridization analysis. Of eight isolates derived from experiments where ΦC31 integrase gene expression was derepressed by the omission of thiamine, seven showed the presence of this ~23 kb band. This same size band hybridized to the ura4 probe. This contrasts with the lack of ura4 hybridization with the parental strain, as expected from its ura4-D18 deletion allele. One of these seven isolates showed additional bands hybridizing to both probes. This candidate appears to have a DNA rearrangement at the leu1 locus in addition to a site-specific recombination event. The leu1 rearrangement was probably catalyzed by the operative *S. pombe* homologous recombination system. The remaining isolate had not experienced a site-specific recombination event and appeared to have gained uracil prototrophy by recombination between pLT45 and pLT43. Of these eight isolates, half were selected as both Ura⁺ and His⁺, but no significant difference was found between this group and the group selected for Ura⁺ only.

From transformation experiments plated in the presence of vitamin B1, an equal number of Ura⁺ transformants was examined by DNA hybridization. The thiamine-repressible Pnmt promoter is expected to limit integrase production, and thereby site-specific integration. Two of the eight Ura⁺ candidates isolated from this low frequency transformation showed a band of 23 kb hybridizing to leu1 and to the ura4 probe. However, since both probes detected an additional band, they do not represent correct integration events, and we grouped them as class b integrants. In the other six isolates, the hybridization patterns are difficult to interpret. In some of them, the 3 kb band was not detected by the leu1 probe, as though the locus has experienced some rearrangement. In many of them, the weak hybridization to ura4 suggests that the Ura⁺ phenotype may not be due to the stable maintenance of pLT45 in the genome.

To ascertain the proportion of transformants maintaining the integrase plasmid in the absence of selection, the blots were re-probed with the integrase gene sequence. Those selected as Ura⁺ His⁺ would be expected to maintain the plasmid, and did so, as the hybridization revealed. Five of the eight isolates selected as Ura⁺ without regard to the His phenotype also gave bands hybridizing to the integrase probe. To confirm that loss of int would not affect stable integration, another set of randomly chosen Ura⁺ cells were grown non-selectively for a number of generations and screened for His⁻ progeny that have lost pLT43. The analysis of eight representative Ura⁺ His⁻ clones showed that all had a single copy of pLT45 precisely integrated at the chromosome-situated attP site. The DNA of these integrants did not hybridize with the integrase probe. In contrast, the background frequency Ura⁺ clones derived by transformation of pLT45 alone gave the parental configuration of hybridizing bands at the leu1 locus and additional faint bands at 5 kb and 7 kb. These observations are consistent with either integration of pLT45 elsewhere in the genome, or maintenance of the plasmid in some cells despite the lack of a *S. pombe* replication origin.

Conservative Site-Specific Recombination

PCR was used to retrieve the attP/attB recombinant junctions from three representative Ura⁺ candidates. One of the hybrid sites, attR (PB') would be flanked by T3 and T7 promoters; the other site, attL (BP') by the T3 promoter and ura4 DNA (FIG. 1C). In each case, primer pairs directed to these sequences amplified a band of the expected size while the original attP (PP') was no longer found. This contrasts with the parental strain FY527attP, where attP, but neither attL nor attR, was detected. The nucleotide sequence of three representative attL and attR PCR products showed the absence of accompanying mutations. Hence, as in bacteria and mammalian cells, ΦC31 mediated site-specific recombination in *S. pombe* is a conservative recombination reaction.

ΦC31 Integrase does not Excise Integrated Molecules

Thorpe and Smith ((1998) *Proc. Natl. Acad. Sci. USA* 95: 5505-5510) did not detect reversal of the ΦC31 integrase reaction by analysis of gel-fractionated DNA fragments. We examined the possibility of a reverse reaction through a genetic selection strategy. The precise integration of pLT45 into FY527attP was confirmed for three clones by Southern analysis; these strains were then re-transformed with pLT43. Excision of pLT45 would result in loss of the ura4⁺ marker; the Ura⁻ phenotype can be scored on plates with 5-FOA (Grimm et al. (1988) *Mol. Gen. Genet.* 215: 81-86). The frequencies of Ura⁻ segregants from cultures of the three Ura⁺ His⁻ progenitors were $5.7 \times 10^{-4}$, $7.1 \times 10^{-4}$ and $5.6 \times 10^{4}$. In contrast, the frequencies of Ura⁻ colonies from the three Ura⁺ His⁺ derivatives were somewhat higher: $1.1 \times 10^{-2}$, $3.8 \times 10^{-3}$ and $2.3 \times 10^{-3}$, respective 19-, 5- and 4-fold increases. When a control vector lacking the integrase gene, pBG2, was used instead, increased rates of 5-FOA resistance were also found: $1.0 \times 10^{-2}$, $1.0 \times 10^{-2}$, and $8.0 \times 10^{-3}$, respectively. The transformation process itself appears mutagenic.

Three Ura⁻ His⁺ clones from each of the three cultures that had been transformed by pLT45 were analyzed by Southern blotting. One isolate had a DNA pattern consistent with stable integration of pLT45 into FY527attP. Therefore, in this clone, the Ura⁻ phenotype was caused by a mutation that did not appreciably alter the restriction pattern, rather than by reversal of the site-specific recombination reaction. The second clone showed a Southern pattern characteristic of FY527attP lacking a pLT45 insertion, the third had a pattern consistent with a mixture of two types of cells, those like FY527attP without a pLT45 insertion, and those like the FY527attP progenitor strain FY527. The latter structure could arise from intrachromosomal homologous recombination between the leu repeats, reversing the insertion of pLT44 (FIG. 1A). If precise excision of the integrated plasmid DNA occurred in the latter two candidates, the attP site would be regenerated; this would be detectable with PCR. The size of the PCR product was that expected for an intact hybrid site, the presence of the hybrid site was confirmed by sequencing the PCR product. These observations are consistent with the idea that deletion of the ura4 gene occurred by some mechanism other than ΦC31-mediated excision.

SUMMARY

The integration of a circular molecule at a single target site was an efficient process yielding precise insertions in nearly all transformants. The few aberrant events we observed are probably largely attributable to the *S. pombe* recombination system acting on the leu1 repetitive DNA. When integrase production was limited through the repression of its promoter, the number of transformants was reduced to near background level. Under these conditions, few of the recovered transformants were derived from ΦC31 site-specific recombination. Functional operation of the ΦC31 site-specific recombination system in eukaryotic cells presents new opportunities for the manipulation of transgenes and chromosomes. The ΦC31 system can be used with selective placement of attB and attP sites to delete, invert or insert DNA. An important feature of this system is that the attB×attP reaction is irreversible in the absence of an excision-specific protein.

Example 2

The ΦC31 Integrase Functions in CHO Cells to Create Stable Integration

This Example describes an experiment in which the ΦC31 integrase was tested for ability to mediate recombination between attB and attP recombination sites in Chinese hamster ovary (CHO) cells.

Methods

The CHO cell line 51YT211 was transfected with the attP-containing plasmid pFY1, which included a selectable marker that confers zeocin resistance (FIG. 2). After being single colony purified twice, six zeocin resistant cell lines were isolated. Analysis by Southern DNA hybridization confirmed that each of the six cell lines had at least one molecule of pFY1 integrated into the genome.

Each of the six cell lines was transfected with the attB-containing plasmid pFY9 and the int-containing plasmid pFY6 to test for site-specific recombination between the attB sites on pFY9 and the attP site on the chromosomal copy of pFY1. As control, the same cell lines were transfected with pFY9, but without the int-containing pFY6. The pFY9 plasmid included a neomycin resistance selectable marker under the control of an SV40 early promoter, as well as a green fluorescent protein (GFP) coding sequence that is not linked to a promoter. Site-specific recombination would thus be expected to place the GFP coding sequence under the control of a human cytomegalovirus promoter that was included in pFY1, resulting in expression of GFP.

Results

Transfection results: Neomycin resistant colonies were placed under the microscope to observe whether the GFP gene is active. A large percentage of the cells transfected with pFY9+pFY6, but only a few of the cells transfected with the pFY9 alone showed GFP activity. This is consistent with site-specific integration of pFY9 when co-transfected with pFY6, and random insertion of pFY9 in the absence of a co-transfected int gene.

PCR analysis was conducted using a primer set that corresponds to Pc (human cytomegalovirus promoter) and GFP (FIG. 2). These primers would be expected to amplify a band of ~0.6 kb corresponding to the integration junction. As neomycin resistant colonies could arise from both site-specific integration and random integration, and that the GFP marker does not confer a selectable trait, it was difficult to obtain pure cultures of integrant clones. Therefore, pools of neomycin resistant cells from each transfected line were subjected to PCR analysis to examine if the integration junction were present among the neomycin resistant cells. A band of the expected size of ~0.6 kb was obtained from two lines. This indicates that the attB×attP recombination junction has formed linking Pc with GFP.

Example 3

ΦC31 Integrase Catalyzes Site-Specific Recombination in CHO Cells

This Example describes a second experiment in which the ΦC31 integrase was tested for ability to integrate a DNA molecule into the chromosome of Chinese hamster ovary (CHO) cells through the recombination between attP and attB sites.

Methods

Plasmid constructs

Chromosomal attB Target Constructs pFY12, pFY14 and pFY15

The plasmid pcDNA3.1/His/lacZ (Invitrogen) was used as a vector backbone. A synthetic oligonucleotide contained different length of the attB site, flanked by HindIII and KpnI sites, was inserted between the HindIII (AAGCTT) and KpnI (GGTACC) sites of pcDNA3.1/His/lacZ.

The plasmid pFY12 contains 90 bp of the attB sequence (AAGCTT gacggtctcg aagccgcggt (SEQ ID NO: 2)

gcgggtgcca gggcgtgccc ttgggctccc cgggcgcgta ctccacctca cccatctggt ccatcatgat GGTACC).

The plasmid pFY14 contained 50 bp of the attB site (AAGCTT gcgggtgcca gggcgtgccc (SEQ ID NO: 3)

ttgggctccc cgggcgcgta ctccacctca

TGGTACC).

The plasmid pFY15 contained 30 bp of attB (AAGCTT ccagggcgtg cccttgggct (SEQ ID NO: 4)

ccccgggcgc ATGGTACC).

Integrating attP Plasmids pFY17, pFY19, pFY20

The hpt gene encoding for resistance to hygromycin, obtained as a 1.6 kb BamHI to KpnI fragment from pED113, was inserted between the BamHI and KpnI sites of pBluescript II SK to generate the control plasmid pBSK-hpt.

A synthetic oligonucleotide containing different lengths of the attP site was inserted between SacI (GAGCTC) and BamHI (GGATCC) sites in pBSK-hpt to generate the following plasmids:
  a) The plasmid pFY17 contains 90 bp ( GAGCTC-gaagcggttt tcgggagtag -tgccccaact gggg- taacct ttgagttctc tcagttgggg gcgtagggtc gccgacatga cacaaggggt-GGATCC) of attP site (SEQ ID NO: 5).
  b) The plasmid pFY19 contains 50 bp of attP site ( GAGCTC-tgccccaact ggggtaacct ttgagttctc tcagttgggg gcgtagggtc-GGATCC) (SEQ ID NO: 6).
  c) The plasmid pFY20 contains 32 bp of attP site (GAGCTC-actggggtaa cctttgagtt ctctcagttgggATCC) (SEQ ID NO: 7).

Integrase Expressing Construct pFY6

An EcoRI to BamHI fragment containing the nearly complete open reading frame of the integrase gene was inserted between the EcoRI and BamHI sites of pcDNA3.1/Zeo(−) (Invitrogen). A synthetic oligonucleotide (GGGCCCGC-CACGATGACA CAAGGGGTTGTGACCGGGGTGGA-CACGTACGCGGGTGCTTACGACCGTCAGTCG CGC-GAGCGCGAGAATTC) (SEQ ID NO: 8) containing a Kozack sequence and the N-terminal amino acid coding sequences of the integrase gene was subsequently inserted between the ApaI and EcoRI sites to reconstruct the open reading frame. This orientation places a complete integrase coding region under the control of the CMV (human cytomegalovirus) promoter in pcDNA3.1/Zeo(−).

Transfection Protocol

The CHO cell line K-1 was transfected with attB target constructs pFY12, pFY14 or pFY15 (FIG. 3). These plasmids harbor the selectable marker for neomycin resistance, and an attB site of various lengths located between Pc (human cytomegalovirus promoter) and the lacZ coding region. Plasmids pFY12, pFY14 and pFY15 contain, respectively, 90, 50 and 30 bp of the attB sequence. Neomycin-resistant cell lines were obtained from consecutive purification of single colonies. Four lines of each construct were used for integration experiments.

Each of the 12 lines was transfected with pFY6, a ΦC31 integrase expression plasmid, along with an integration vector, pFY17, pFY19, or pFY20. The plasmids pFY17, pFY19 and pFY20 harbor an attP sequence of lengths 90, 50 and 32 bp, respectively. The attP sequence is situated upstream of the hpt open reading frame, which encodes hygromycin phosphotransferase, an enzyme that confers resistance to hygromycin. There is no promoter upstream of the attP-hpt segment and hpt is therefore not expressed unless the plasmid integrates into the genome in such a way that the hpt coding region fuses with a genomic promoter. For control, pBSK-hpt was used to monitor the frequency of promoter fusion to hpt. The plasmid pBSK-hpt is identical to pFY17, pFY19, and pFY20 except it lacks an attP sequence. The recombination between attP and attB sites is expected to insert the integration vector into the chromosome target to generate a Pc-attL-hpt linkage. Expression of hpt will confer resistance to hygromycin.

Results

Transfection results: Hygromycin resistant colonies were scored for each integration plasmid which was transfected into the 12 cell lines (Table 2). From $1\times10^6$ cells plated, pBSK-hpt transfections failed to produce a significant number of resistant colonies. This indicates that the frequency of the hpt coding region fusing to a genomic promoter is extremely low. In contrast, pFY17, pFY19 and pFY20 yielded up to a thousand fold higher number of hygromycin resistant colonies, depending on the particular integration plasmid and the particular cell line. Higher numbers of hygromycin resistant colonies were produced from the transfection of pFY19 or pFY17 into FY12 lines. This indicates that the recombination between longer attB and attP sequences is more efficient than the recombination between shorter attB and attP sites.

PCR was used to detect the expected ~0.8 Kb junction band from representative colonies. Primers corresponding to the human cytomegalovirus promoter and the hpt coding region amplified a PCR product of the expected size (0.8 kb). This indicates that Pc is linked to the hpt coding region, consistent with recombination between the genomic attB site and the plasmid attP sequence.

Example 4

Figure 4:
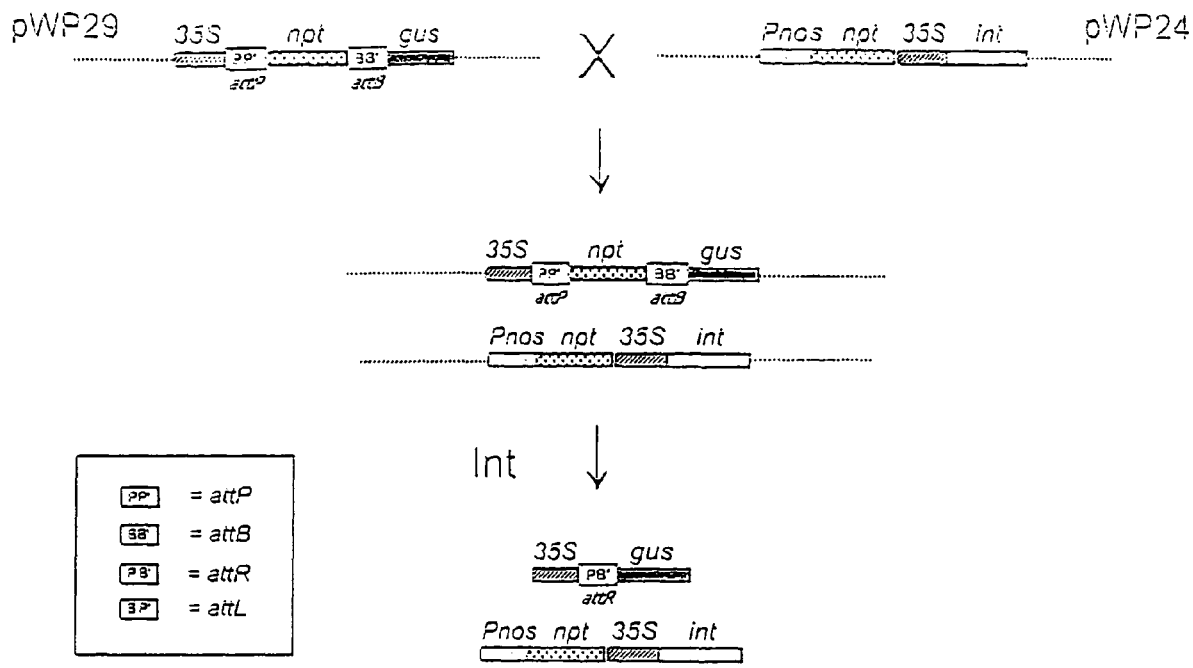
FIG. 4 shows a schematic diagram of an experiment which demonstrates that Φ31 integrase catalyzes the excision of a DNA flanked by attB and attP sites from the tobacco genome.

The ΦC31 Integrase Functions in Plant Chromosomes to Recombine attP and attB Sites This example describes an experiment in which the ΦC31 integrase was tested for ability to recombine attP and attB sites that are present in a plant chromosome. The constructs and strategy for this experiment are shown in FIG. 4.

TABLE 2

Number of hygromycin resistant colonies per $1 \times 10^6$ transfected cells.

| Target cell lines | Integration plasmids | | | |
|---|---|---|---|---|
| | pFY17 (90 bp AttP) | pFY19 (50 bp AttP) | pFY20 (32 bp AttP) | pBSK-hpt (no attP site) |
| (attB-90) | | | | |
| FY12-1 | 256 | 856 | 275 | 0 |
| FY12-2 | 976 | 896 | 185 | 0 |
| FY12-3 | 246 | 976 | 114 | 2 |
| FY12-4 | 964 | 896 | 327 | 0 |
| (attB-50) | | | | |
| FY14-3 | 23 | 240 | 45 | 0 |
| FY14-7 | 96 | 245 | 67 | 0 |
| FY14-8 | 21 | 135 | 49 | 2 |
| FY14-9 | 89 | 255 | 78 | 1 |
| (attB-30) | | | | |
| FY15-1 | 0 | 24 | 0 | 0 |
| FY15-2 | 0 | 345 | 34 | 0 |
| FY15-3 | 55 | 455 | 23 | 1 |
| FY15-4 | 0 | 0 | 0 | 0 |

Methods

The construct pWP29 contains the fragment consisting of 35S-attP-npt-attB-gus, flanked by RB and LB, where 35S is the cauliflower mosaic virus promoter, npt is the coding region for neomycin phosphotransferase, and gus is the coding-region for glucuronidase. RB and LB are the right and left *Agrobacterium* T-DNA border sequences, respectively. The attP site between 35S and npt serves as a non-translated leader sequence. Transcription of npt by 35S confers resistance to kanamycin. The gus coding region is not transcribed due to the lack of an upstream promoter.

A second construct used for plant transformation is pWP24. This construct contains the fragment Pnos-npt-35S-int, flanked by RB and LB, where Pnos is the nopaline synthase promoter, and int is the ΦC31 integrase coding region. Both npt and int are transcribed from their respective upstream promoters.

If the two constructs were present in the same genome, the expression of int from the pWP24 bearing chromosome would be expected to produce functional ΦC31 integrase to catalyze the recombination between attB and attP sites situated on the pWP29-bearing chromosome. The recombination event would be expected to delete the npt gene from the pWP29 construct and fuse 35S to gus. The resulting configuration would be 35S-attR-gus, where attR is a hybrid site formed by the recombination between attP and attB, also designated as PB' (FIG. 4). The deletion of npt brings gus under the transcription of 35S and would be expected to yield plants with GUS enzyme activity. This activity can be detected through histochemical staining of the plant tissue.

Results

A transient expression assay was conducted to determine whether pWP29 was functional for recombination. Through the biolistics-mediated delivery of naked DNA, pWP29 was cointroduced with pWP8 into maize BMS cells. The construct pWP8 has the integrase gene fused behind the maize ubiquitin promoter for expression in monocot cells. Blue spots were observed when both plasmids were co-introduced, but were not found if only one of the plasmids was used. This indicated that site-specific recombination took place in maize cells and that the attP and attB sites in pWP29 were functional sites.

Kanamycin resistant tobacco plants were regenerated by *Agrobacterium*-mediated transformation using pWP29 or pWP24. Another transient expression assay was conducted to determine whether the pWP24 lines produced functional integrase. The construct pWP29 was introduced into the pWP24 plants through biolistics mediated delivery of naked DNA. Cells that take up the pWP29 DNA would be expected to express GUS enzyme activity as a result of the formation of a 35S-attR-gus configuration. Indeed, two lines, 24.3 and 24.4 yielded blue spots consistent of functional integrase-mediated site-specific recombination between the attP and attB sites.

These two pWP24 integrase lines were crossed to pWP29 tester lines to produce progeny with the chromosomes carrying pWP29 and pWP24 in the same genome. Table 3 summarizes the results from the genetic crosses between integrase (24.3, 24.4) and tester lines (29.2, 29.4, 29.5, 29.19). In each case, representative progeny seedlings were germinated in the absence of selection and histochemically stained for GUS enzyme activity. The table lists the number of progeny that stained blue. As the primary transformed pWP24 and pWP29 lines are hemizygous for their respective transgene, only a quarter of the progeny would be expected to carry both transgene types. The sample sizes were small, so an apparent deviation from the expected frequency is not unusual.

TABLE 3

Progeny that showed gus expression from histochemical staining.

| Male Donor plant line | Female Recipient plant line | Number of progeny stained for gus activity | Number of progeny that show gus activity. | % positive for gus activity |
|---|---|---|---|---|
| 24.3+ | 29.2 | 38 | 11 | 29% |
| 29.2 | 24.3+ | 38 | 1 | 2.6% |
| 29.4 | 24.3+ | 18 | 3 | 16% |
| 24.3+ | 29.5 | 38 | 4 | 10% |
| 29.5 | 24.3+ | 26 | 0 | 0 |
| 24.4 | 29.2 | 38 | 7 | 19% |
| 29.2 | 24.4+ | 38 | 7 | 19% |
| 29.4 | 24.4+ | 19 | 8 | 42% |
| 24.4+ | 29.5 | 38 | 17 | 45% |
| 29.5 | 24.4+ | 20 | 6 | 30% |
| 29.19 | 24.4+ | 18 | 7 | 39% |

The intensity of staining varied depending on the combination of lines used as parental lines. Those with progeny with a greater proportion of the tissue staining blue indicate that the recombination event was more efficient. Conversely, those yielding progeny with less uniform staining indicate that the recombination event was less efficient. This variation among the different progeny pools is probably due to effects caused by the position of integration of the transgenes. Of the two integrase lines, 24.4 appears more efficient in promoting site-specific recombination. This is probably due to a higher level of int gene expression. Staining patterns produced by crossing 24.4 to 29.4 and 29.19 are consistent with the experimental design that int promoted site-specific recombination of attB and attP results in the activation of gus gene activity.

Example 5

Figure 5:
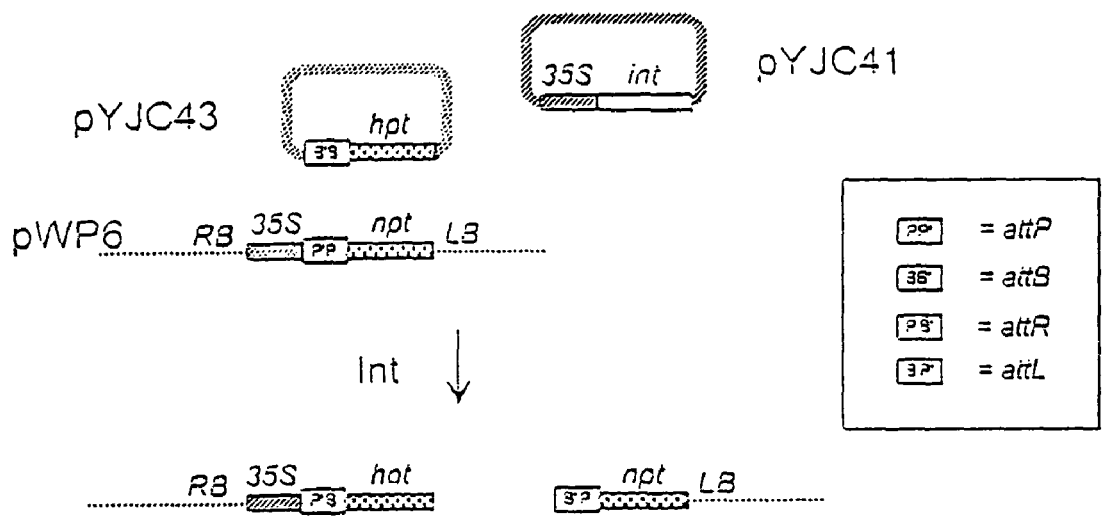
FIG. 5 shows a schematic diagram of an experiment in which ΦC31 integrase was shown to catalyze integration of a transgene into the tobacco genome.

ΦC31 Integrase Catalyzes Integration of a Circular Plasmid into a Plant Chromosome This example describes an experiment in which the ΦC31 integrase was tested for ability to insert a circular plasmid molecule into the plant chromosome through attP×attB site-specific recombination. This experiment is diagrammed in FIG. 5.

Methods

The target construct pWP6 contains the fragment consisting of 35S-attP-npt, flanked by RB and LB. The attP site between 35S and npt serves as a non-translated leader sequence. Transcription of npt by 35S confers resistance to kanamycin.

The integrating construct pYJC43 has the fragment attB-hpt, where hpt codes for resistance to hygromycin. The integrase expression construct is pYJC41, in which 35S transcribes int.

The target construct pWP6 was placed into a plant chromosome through random integration of pWP6 DNA. Kanamycin resistant plants harboring a single copy of the pWP6 transgene are then subsequently transformed with pYJC43 and pYJC41. The transient expression of int from pYJC41 was expected to catalyze the recombination between the attB site of pYJC43 and the chromosomally-situated attP site of the pWP6 transgene. The specific recombination between attB and attP sites would insert the pYJC43 circular molecule into the chromosome to generate a 35S-attL-hpt linkage. Note that because the attP and attB sites are depicted in the inverted orientation, the attL site will likewise be in an inverted orientation, or designated P'B, the same as BP' in the drawn in an inverted orientation. A functional 35S-attL-hpt linkage would confer a hygromycin resistance phenotype.

Results

Kanamycin resistant tobacco plants harboring pWP6 were obtained through *Agrobacterium*-mediated transformation. Southern hybridization analysis detected one line that harbors a single copy of the pWP6 transgene. Progeny from this line, WP6.1, were germinated aseptically and protoplasts were made from these plants. The protoplasts were transformed by the combination of pYJC43 and pYJC41 DNA by the polyethylene glycol method for direct DNA transformation. The protoplasts were then imbedded into agarose and cultured to form calli in the presence of hygromycin. The rate of callus formation in the absence of hygromycin selection was $4 \times 10^{-4}$. This is about 10 fold lower than usual, but is within the range of variability observed in protoplast transformation experiments. In the presence of hygromycin selection, the rate of callus formation was $7 \times 10^{-5}$. This indicates that about 18% of the calli that regenerated from protoplasts contained the integration vector at the target site. When the integrase construct pYJC41 was excluded from the transformation, the rate of callus formation was $<1 \times 10^{-5}$. The higher frequency of hygromycin resistant calli produced by inclusion of the integrase expressing plasmid pYJC41 is consistent with the integrase promoted site-specific integration of pYJC43 into the chromosomal attP target.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A plant or yeast eukaryotic cell that comprises
a prokaryotic recombinase polypeptide or a nucleic acid that encodes the prokaryotic recombinase, wherein the recombinase is capable of mediating site-specific recombination in the eukaryotic cell between an attB recombination site and an attP recombination site to form an attL and an attR site; and wherein the recombinase is not capable of mediating in the eukaryotic cell recombination between the attL site and the attR site, wherein the recombinase is a bacteriophage ΦC31 integrase; and only one attP or only one attB recombination site of bacteriophage ΦC31 integrase integrated in its genome.

2. The eukaryotic cell of claim 1, wherein the cell comprises a nucleic acid that comprises a coding sequence for the recombinase polypeptide, which coding sequence is operably linked to a promoter that mediates expression of the recombinase-encoding polynucleotide in the eukaryotic cell.

3. The eukaryotic cell of claim 2, wherein the nucleic acid further comprises a selectable marker.

4. The eukaryotic cell of claim 2, wherein the promoter is an inducible or a repressible promoter.

5. The eukaryotic cell of claim 1, wherein the cell is a yeast cell.

6. The eukaryotic cell of claim 1, wherein the eukaryotic cell is a plant cell.

7. A plant or yeast eukaryotic cell that comprises:
an attP or attB recombination site of bacteriophage ΦC31 integrase integrated in its genome; and
a non-genomic nucleic acid comprising a heterologous nucleic acid or a transgene, and only one attP site of bacteriophage ΦC31 integrase if the cell has the genomic attB site or only one attB site of bacteriophage ΦC31 integrase if the cell has the genomic attP site; wherein the eukaryotic cell further comprises a ΦC31 integrase polypeptide.

8. The eukaryotic cell of claim 7, wherein the non-genomic nucleic acid comprises the transgene.

9. The eukaryotic cell of claim 7, wherein the eukaryotic cell comprises a nucleic acid that comprises a polynucleotide that encodes the ΦC31 integrase polypeptide.

10. The eukaryotic cell of claim 9, wherein the nucleic acid further comprises a selectable marker.

11. The eukaryotic cell of claim 9, wherein the nucleic acid further comprises an inducible promoter which controls expression of the ΦC31 integrase-encoding polynucleotide in the cell.

12. The eukaryotic cell of claim 7, wherein the plant is a dicot or a monocot.

13. A eucaryotic somatic cell in culture comprising:
a prokaryotic recombinase polypeptide or a nucleic acid that encodes the prokaryotic recombinase, wherein the recombinase is capable of mediating site-specific recombination in the eukaryotic cell between an attB recombination site and an attP recombination site to form an attL and an attR site, and is not capable of mediating in the eukaryotic cell recombination between the attL site and the attR site;
the attP or attB recombination site integrated in its genome;
a non-genomic nucleic acid comprising a transgene or a heterologous nucleic acid and only one attP site if the cell has the genomic attB site or only one attP site if the cell has the genomic attB site;
wherein the recombinase is a bacteriophage ΦC31 integrase and the attP and attB sites are bacteriophage ΦC31 integrase recombination sites.

14. A method for obtaining site-specific recombination in a eukaryotic cell, the method comprising:
providing a eukaryotic cell that comprises an attB recombination site or an attP recombination site of bacteriophage ΦC31 integrase integrated in its genome and a non-genomic nucleic acid comprising a transgene or a heterologous nucleic acid and only one attP site if the cell has the genomic attB site or only one attP site if the cell has the genomic attB site;
contacting the attB and the attP recombination sites with a prokaryotic recombinase polypeptide, resulting in recombination between the recombination sites, thereby forming an attR and an attL recombination site;
wherein the recombinase polypeptide can mediate site-specific recombination between the attB and attP recombination sites, but cannot mediate recombination between the attR and attL recombination sites;

wherein the recombinase is-a bacteriophage ΦC31 integrase.

15. The method of claim 14, wherein the eukaryotic cell is selected from the group consisting of a yeast cell, a fungal cell, a plant cell, an insect cell and an animal cell.

16. The method for obtaining site-specific recombination in a eukaryotic cell, the method comprising:
providing a eukaryotic cell that comprises an attB recombination site and-an attP recombination site of bacteriophage ΦC31 integrase, wherein the attB recombination site and the attP recombination site are present on a single nucleic acid molecule;
contacting the attB and the attP recombination sites with a prokaryotic recombinase polypeptide, resulting in recombination between the recombination sites, thereby forming an attR and an attL recombination site;
wherein the recombinase polypeptide can mediate site-specific recombination between the attB and attP recombination sites, but cannot mediate recombination between the attR and attL recombination sites; and wherein the recombinase is-a bacteriophage ΦC31 integrase.

17. The method of claim 16, wherein the attB recombination site and the attP recombination site are in a direct orientation and the recombination results in excision of the portion of the nucleic acid molecule that lies between the attB and attP recombination sites.

18. The method of claim 16, wherein the attB recombination site and the attP recombination site are in an inverted orientation and the recombination results in inversion of the portion of the nucleic acid molecule that lies between the attB and attP recombination sites.

19. The method of claim 4, wherein the eukaryotic cell comprises a polynucleotide that encodes the recombinase polypeptide.

20. A plant regenerated from a plant eucaryotic cell of claim 7.

* * * * *

UNITED STATES PATENT AND TRADEMARK OFFICE
CERTIFICATE OF CORRECTION

PATENT NO.         : 8,129,598 B2                                         Page 1 of 1
APPLICATION NO.    : 10/721980
DATED              : March 6, 2012
INVENTOR(S)        : Ow et al.

It is certified that error appears in the above-identified patent and that said Letters Patent is hereby corrected as shown below:

On the Title Page:

In the References Cited section, item (56), page 3, first column, line 44, under the OTHER PUBLICATIONS subsection: please insert --"-- before "Site-specific" and please insert --"-- after "applications,".

In the References Cited section, item (56), page 3, second column, line 49, under the OTHER PUBLICATIONS subsection: before "C31 integrace," please insert --φ--.

In the References Cited section, item (56), page 4, second column, line 2, under the OTHER PUBLICATIONS subsection: please delete "γδresolvase" and insert --γδ resolvase--.

In the Claims:

Claim 19, Column 32, Line 15: please delete "claim 4" and insert --claim 14--.

Signed and Sealed this
Nineteenth Day of June, 2012

David J. Kappos
*Director of the United States Patent and Trademark Office*